United States Patent [19]
Hayashi et al.

[11] Patent Number: 5,932,750
[45] Date of Patent: Aug. 3, 1999

[54] CATALYSTS FOR PARTIAL OXIDATION OF HYDROCARBONS AND METHOD OF PARTIAL OXIDATION OF HYDROCARBONS

[75] Inventors: Toshio Hayashi, Kobe; Masahiro Wada, Nishinomiya; Masatake Haruta, Ikeda; Susumu Tsubota, Ashiya, all of Japan

[73] Assignees: Agency of Industrial Science and Technology, Tokyo; Nippon Shokubai Co., Ltd., Osaka, both of Japan

[21] Appl. No.: 08/945,989

[22] PCT Filed: Mar. 18, 1997

[86] PCT No.: PCT/JP97/00869

§ 371 Date: Nov. 10, 1997

§ 102(e) Date: Nov. 10, 1997

[87] PCT Pub. No.: WO97/34692

PCT Pub. Date: Sep. 25, 1997

[30] Foreign Application Priority Data

Mar. 21, 1996 [JP] Japan .................................. 8-064370
Mar. 3, 1997 [JP] Japan .................................. 9-048221

[51] Int. Cl.[6] .................................................. C07D 301/04
[52] U.S. Cl. ........................................... 549/523; 502/243
[58] Field of Search .................................. 568/360, 401; 549/523, 533; 502/243

[56] References Cited

U.S. PATENT DOCUMENTS

| | | |
|---|---|---|
| 4,990,632 | 2/1991 | Ramachandran et al. . |
| 5,008,412 | 4/1991 | Ramachandran et al. . |
| 5,525,741 | 6/1996 | Sugita et al. . |
| 5,573,989 | 11/1996 | Sugita et al. . |
| 5,623,090 | 4/1997 | Haruta et al. . |

FOREIGN PATENT DOCUMENTS

| | | | |
|---|---|---|---|
| 51-5357 | 2/1976 | Japan . | |
| 4-330938 | 11/1992 | Japan . | |
| 4-352771 | 12/1992 | Japan . | |
| 7-8797 | 1/1995 | Japan . | |
| WO 98/00413 | 1/1998 | WIPO | 549/523 |
| WO 98/00414 | 1/1998 | WIPO | 549/523 |
| WO 98/00415 | 1/1998 | WIPO | 549/523 |

*Primary Examiner*—James H. Reamer
*Attorney, Agent, or Firm*—Nixon & Vanderhye P.C.

[57] ABSTRACT

A partially-oxidizing catalyst for hydrocarbon contains gold, titanium oxide and a carrier whose specific surface area is not less than 50 $m^2/g$. The carrier is preferably made from silicon oxide and/or aluminum oxide. The content of gold in the catalyst is preferably set in the range of 0.005 to 5 % by weight. Further, another partially-oxidizing catalyst for a hydrocarbon contains gold, a titanium-containing metal oxide, and at least one element selected from the group consisting of an alkaline metal, an alkaline-earth metal and thallium. With these compositions, it becomes possible to provide a partially-oxidizing catalyst for a hydrocarbon having superior activity and selectivity in partially oxidizing the hydrocarbon in the presence of hydrogen and oxygen. Moreover, a partially-oxidizing method for a hydrocarbon is used for partially oxidizing the hydrocarbon by using any of the above-mentioned partially-oxidizing catalysts in the presence of hydrogen and oxygen. This method makes it possible to manufacture an epoxide from a hydrocarbon of the olefin family and also to manufacture an alcohol and/or a ketone from a saturated hydrocarbon, with high selectivity and high conversion.

38 Claims, No Drawings

CATALYSTS FOR PARTIAL OXIDATION OF HYDROCARBONS AND METHOD OF PARTIAL OXIDATION OF HYDROCARBONS

FIELD OF THE INVENTION

The present invention relates to a partially-oxidizing catalyst for partially oxidizing a hydrocarbon and a method for partially oxidizing hydrocarbon by which an alcohol and/or a ketone can be obtained from a saturated hydrocarbon and an epoxide can be obtained from a hydrocarbon of the olefin family (an unsaturated hydrocarbon), by partially oxidizing the hydrocarbon by using the partially-oxidizing catalyst in the presence of oxygen and hydrogen.

More specifically, the present invention relates to a partially-oxidizing catalyst for a hydrocarbon with a titanium-containing metal oxide having gold deposited thereon, which is preferably used as a catalyst for manufacturing an epoxide from a hydrocarbon of the olefin family and which is also preferably used as a catalyst for manufacturing an alcohol and/or a ketone from a saturated hydrocarbon, and also concerns a method for partially oxidizing hydrocarbon by using the partially-oxidizing catalyst, which is suitable for manufacturing an alcohol and/or a ketone from a saturated hydrocarbon.

BACKGROUND OF THE INVENTION

Conventionally, with respect to partially-oxidizing methods for hydrocarbon, processes for directly manufacturing an epoxide by partially oxidizing a hydrocarbon of the olefin family have been carried out; however, in most of these processes, oxidizers, such as hydrogen peroxide, organic peracids, and chlorine compounds, are used.

In contrast, processes for transforming hydrocarbons into oxygen-containing compounds by using oxygen, such as, for example, processes for directly manufacturing epoxides from hydrocarbons of the olefin family through a partially-oxidizing reaction using oxygen, have been considered as a very prospective technique since oxygen, which is inexpensive as compared with the above-mentioned oxidizers, is used.

However, it is generally considered to be difficult to directly obtain an alcohol and a ketone that are useful compounds from a saturated hydrocarbon and also to directly obtain an epoxide from an unsaturated hydrocarbon except for rare exceptions, and these practices have hardly been carried out except for a manufacturing method for ethylene oxide.

In particular, with respect to methods for manufacturing propylene oxide by oxygen-oxidizing propylene and catalysts used therein, many suggestions have been made; however, none of these methods have been successfully put into practice since conventional commonly-used catalysts raise problems in performances such as low selectivity.

In order to solve these problems, direct-oxidizing methods, etc., such as the chlorohydrin method, the HALCON method, and the acetyl-hydroperoxide method, have generally been used as the methods for manufacturing propylene oxide by oxygen-oxidizing propylene. However, these manufacturing methods raise other problems in which two reaction processes (two stages) are required and by-products (additional produces) are produced.

For this reason, simpler, more effective manufacturing methods have been demanded, and various methods for manufacturing propylene oxide by directly oxygen-oxidizing (partially oxidizing) propylene that is a hydrocarbon of the olefin family and catalysts used for the manufacturing methods have been proposed.

For example, Japanese Laid-Open Patent Publication No. 97378/1995 (Tokukaihei 7-97378) discloses a method for manufacturing olefin oxide (an epoxide) from olefin (an unsaturated hydrocarbon) in a gaseous phase by using as a catalyst crystalline silicate (silicate) on which metallic salt of nitric acid, such as silver nitrate, is deposited.

Further, Japanese Laid-Open Patent Publication No. 352771/1992 (Tokukaihei 4-352771) discloses a method for manufacturing propylene oxide from propylene in a liquid phase by using a catalyst made of a metal of the VIII family and crystalline titano-silicate.

However, since the catalysts used in these manufacturing methods are inferior in catalyst performances such as activity and selectivity, it has to be said that the above-mentioned conventional methods fail to provide practical manufacturing methods for epoxides.

For this reason, inventors and other personnel of the present application have earnestly made research into a partially-oxidizing method for a hydrocarbon by which an alcohol and/or a ketone can be obtained from a saturated hydrocarbon and an epoxide can be obtained from an unsaturated hydrocarbon, by partially oxidizing the hydrocarbon in the presence of oxygen and hydrogen, and a catalyst that is preferably used for the above-mentioned partially-oxidizing method for hydrocarbon. Consequently, it has been discovered that a catalyst containing gold and titanium oxide is preferably used for the partially-oxidizing method for hydrocarbon.

Accordingly, in Japanese Laid-Open Patent Publication No. 127550/1996 (Tokukaihei 8-127550), the inventors and other personnel of the present application have disclosed a method for manufacturing an epoxide by oxygen-oxidizing an unsaturated hydrocarbon in the presence of molecular hydrogen and a catalyst containing gold and titanium oxide. With this method, it is possible to obtain epoxides with high selectivity.

However, the above-mentioned catalyst, provided by the inventors and other personnel of the present application, is found to be inferior in the activity although it has high selectivity. For this reason, in the case when, for example, the catalyst is applied to a manufacturing method for an epoxide, the conversion of the unsaturated hydrocarbon to the epoxide is as low as not more than 3%, and the amount of hydrogen to be burned is high.

In the reaction using the above-mentioned gold-titania catalyst, there is a tendency in which although the consumption of hydrogen is increased by increasing the reaction temperature (especially, at not less than 100° C.), it is difficult to increase the product activity of the partially-oxidized product, such as an epoxide, and the amount of product of the partially-oxidized product does not increase or reduces. In other words, in the above-mentioned catalyst, the maximum level of the catalyst performance, which is achieved by optimizing the reaction conditions such as reaction temperature, is comparatively low, and further improvements are required to put the above-mentioned reaction into practical use.

The first objective of the present invention that has been devised to solve the above-mentioned problems is to provide a partially-oxidizing catalyst for hydrocarbon which has superior activity and selectivity in carrying out a reaction for partially oxidizing the hydrocarbon in the presence of hydrogen and oxygen and which can make the partially-oxidizing reaction put into practical use with high selectivity and high conversion.

Moreover, the second objective of the present invention is to provide a partially-oxidizing method for hydrocarbon which allows to obtain an epoxides from a hydrocarbon of the olefin family (an unsaturated hydrocarbon) and also to obtain an alcohol and/or a ketone from a saturated hydrocarbon, with high selectivity and high conversion.

DISCLOSURE OF THE INVENTION

The inventors and other personnel of the present invention have earnestly made research into a partially-oxidizing catalyst for hydrocarbon. As a result, it has been confirmed that a partially-oxidizing catalyst for hydrocarbon, which contains gold, titanium oxide, and a carrier whose specific surface area is not less than 50 m$^2$/g, has superior activity and selectivity in carrying out a reaction for partially oxidizing hydrocarbon under the presence of hydrogen and oxygen.

In other words, in order to achieve the above-mentioned first objective, the first partially-oxidizing catalyst for hydrocarbon of the present invention is characterized in that it contains gold, titanium oxide, and a carrier whose specific surface area is not less than 50 m$^2$/g.

Different from the aforementioned gold-titania catalyst, the partially-oxidizing catalyst having the above-mentioned composition contains such a carrier with high specific surface area that the activity for producing a partially-oxidized product such as epoxides is improved in response to an increase in the reaction temperature even under a reaction temperature of not less than 100° C. Therefore, in the above-mentioned partially-oxidizing catalyst, it is possible to improve the maximum level of the catalyst performance (activity) that is achieved by optimizing the reaction conditions such as reaction temperatures, and consequently to attain a level in which practical use is achieved.

Moreover, the inventors and other personnel of the present application have further made research in earnest into a partially-oxidizing catalyst for hydrocarbon that is used for a reaction for partially oxidizing hydrocarbon in the presence of hydrogen and oxygen. As a result, it has been confirmed that a partially-oxidizing catalyst, which contains gold, a titanium-containing metal oxide and at least one element selected from the group consisting of alkaline metal, alkaline-earth metal and thallium, has superior activity and selectivity in carrying out the reaction for partially oxidizing hydrocarbon in the presence of hydrogen and oxygen.

In other words, in order to achieve the first objective, the second partially-oxidizing catalyst for hydrocarbon of the present invention is characterized in that it contains gold, a titanium-containing metal oxide and at least one element selected from the group consisting of alkaline metal, alkaline-earth metal and thallium.

The above-mentioned composition makes it possible to provide a partially-oxidizing catalyst which has superior activity and selectivity in carrying out a reaction for partially oxidizing hydrocarbon in the presence of hydrogen and oxygen. Therefore, the partially-oxidizing catalyst having the above-mentioned composition is preferably used as a catalyst for manufacturing epoxides by partially oxidizing hydrocarbon of the olefin family, and also as a catalyst for manufacturing alcohols and/or ketones by partially oxidizing saturated hydrocarbon.

In addition, with the above-mentioned composition, the one element, selected from the group consisting of alkaline metal, alkaline-earth metal and thallium, makes it possible to suppress deterioration with time, thereby providing a catalyst having superior stability in life time.

Furthermore, the inventors and other personnel of the present application have further made research in earnest into a partially-oxidizing method for hydrocarbon for partially oxidizing hydrocarbon in the presence of hydrogen and oxygen. As a result, it has been confirmed that the application of the above-mentioned first or second partially-oxidizing catalyst makes it possible to obtain alcohols and/or ketones from saturated hydrocarbon with high selectivity and high conversion, and also to obtain epoxides from hydrocarbon of the olefin family (unsaturated hydrocarbon) with high selectivity and high conversion, by partially oxidizing the hydrocarbon in the presence of oxygen and hydrogen; thus, the present invention is completed.

In other words, in order to achieve the second objective, the first partially-oxidizing method for hydrocarbon of the present invention is characterized in that it partially oxidizing hydrocarbon in the presence of hydrogen and oxygen by using the first partially-oxidizing catalyst for hydrocarbon.

Further, in order to achieve the second objective, the second partially-oxidizing method for hydrocarbon of the present invention is characterized in that it partially oxidizing hydrocarbon in the presence of hydrogen and oxygen by using the second partially-oxidizing catalyst for hydrocarbon.

With the first and second methods, it is possible to carry out a reaction for partially oxidizing hydrocarbon with high selectivity and high conversion. In other words, it is possible to manufacture epoxides from hydrocarbon of the olefin family (unsaturated hydrocarbon), and also to manufacture alcohols and/or ketones from saturated hydrocarbon with high selectivity and high conversion respectively.

In addition, the first method makes it possible to reduce the amount of hydrogen to be burned. Further, since the catalyst having superior stability in lifetime is used, the second method makes it possible to respectively manufacture epoxides, alcohols and/or ketones stably for a long period, with high selectivity and high conversion.

The following description will discuss the present invention in detail.

The first partially-oxidizing catalyst for hydrocarbon (hereinafter, referred to simply as catalyst (1)) contains gold, titanium oxide (titania) and a carrier whose specific surface area is not less than 50 m$^2$/g.

With respect to the above-mentioned gold, particles having a particle-diameter in nanometer (nm) sizes (not more than 10 nanometer in diameter), that is, so-called ultrafine particles, are preferably used. The carrier amount (content) of gold in catalyst (1) is preferably set at not less than 0.001% by weight, more preferably set in the range of 0.005% to 5% by weight, most preferably set in the range of 0.01% to 1.0% by weight, and by far the most preferably set in the range of 0.05% to 0.2% by weight.

A carrier amount of gold below 0.001% by weight is not preferable because it causes degradation in the activity of catalyst (1). Further, a carrier amount of gold exceeding 5% by weight is not preferable because no further improvements in the activity of catalyst (1) are obtained as compared with the case in which gold is deposited within the above-mentioned range and because gold is wastefully used.

The crystal structure of the titanium oxide is not particularly limited; however, that of amorphous type or anatase type is preferably used. Further, titanium oxide may be provided as a complex material with other oxide. In catalyst (1), the carrier amount (content) of titanium oxide is preferably set in the range of 0.1% to 20% by weight, and more preferably set in the range of 0.5% to 10% by weight.

Therefore, in particular, it is preferable to set the content of gold in the range of 0.005% to 5% by weight, and also to set the content of titanium oxide in the range of 0.1% to 20% by weight.

A carrier amount of titanium oxide below 0.1% by weight is not preferable since it causes degradation in the activity of catalyst (1). Further, a carrier amount of titanium oxide exceeding 20% by weight is not preferable because no further improvements in the activity of catalyst (1) is obtained as compared with the case in which titanium oxide is deposited within the above-mentioned range.

The activity of catalyst (1) can be improved by fixing (allowing to deposit) gold and titanium oxide onto a carrier whose specific surface area is not less than 50 $m^2/g$. More specifically, the following materials are, for example, listed as the above-mentioned carrier: silicon oxide, aluminum oxide, zirconium oxide, and complex materials thereof; crystalline metallosilicate such as zeolitic; and other materials. Among these materials, silicon oxide and/or aluminum oxide are more preferable, and silicon oxide is most preferable.

Moreover, the crystal structure, shape, size, etc. of the carrier are not particularly limited; however, it is preferable to set its specific surface area at not less than 50 $m^2/g$, and more preferably at not less than 100 $m^2/g$. By setting the specific surface area at not less than 50 $m^2/g$, the performance of catalyst (1) is further improved. In other words, since side reactions, such as serial oxidation, are further suppressed, it is possible to partially oxidizing hydrocarbon more effectively, and also to further reduce the amount of hydrogen to be burned.

In the case when silicon oxide and aluminum oxide are combinedly used, the ratio of the two materials is not particularly limited. Further, in the present invention, the expression "containing silicon oxide and aluminum oxide" is defined as including cases "containing zeolite (aluminosilicate) and silica alumina.

Moreover, catalyst (1) may further include a carrier whose specific surface area is less than 50 $m^2/g$ to such a degree as not to impair the activity. In other words, catalyst (1) of the present invention is constituted by a carrier (hereinafter, referred to simply as a carrier) whose specific surface area is not less than 50 $m^2/g$, gold and titanium oxide that are deposited on the carrier. Additionally, titanium oxide may be deposited on the carrier by carrying out a calcination process after a titanium compound such as a complex has been deposited on the carrier.

With respect to methods for preparing catalyst (1), that is, fixing methods for fixing gold and titanium oxide onto the carrier, for example, the deposition-precipitation method, the coprecipitation method, the impregnation method and other methods are listed; however, the present invention is not particularly limited thereby. Further, powder of gold and/or gold compound and powder of titanium oxide may be blown onto the carrier so that gold and titanium oxide are allowed to adhere to the carrier and to be fixed thereon. With this fixing method, gold and titanium oxide are firmly fixed onto the carrier with a comparatively uniform distribution.

In the case when gold and titanium oxide are separately deposited onto the carrier, it is preferable to allow gold to be deposited after titanium oxide has been deposited. Further, after allowing gold to be deposited on titanium, the titanium oxide having gold deposited thereon may be deposited on the carrier. Moreover, titanium oxide may be deposited onto a carrier such as silicon oxide or aluminum oxide by dispersing it thereon to form a so-called coating or a so-called island structure.

More specifically, with respect to fixing methods for fixing gold onto a carrier, for example, the following method may be adopted: After titanium oxide has been deposited on the carrier, the carrier is immersed into an aqueous solution containing a gold compound so that gold deposit is precipitated onto the carrier. The gold compound is not particularly limited, as long as it is water soluble. The temperature of the aqueous solution is preferably set in the range of 30° C. to 80° C., although it is not particularly limited. In this case, the pH of the aqueous solution may be adjusted in the range of 6 to 10, if necessary, and in order to increase the carrier amount of gold in catalyst (1) or in order to reduce the particle diameter of ultrafine gold particles, a surface active agent, carbonate and/or a salt thereof may be added to the aqueous solution. More specifically, with respect to the surface active agent, a long-chain alkyl (aryl) sulfonic acid whose carbon number is not less than 8 and a salt thereof, and a long-chain alkyl (aryl) carbonate and a salt thereof are adopted. Here, with respect to the carbonate and a salt thereof, for example, citric acid and its sodium salt and magnesium salt are adopted.

As described above, the first partially-oxidizing catalyst for hydrocarbon of the present invention contains gold, titanium oxide and a carrier whose specific surface area is not less than 50 $m^2/g$. With this composition, it is possible to provide a partially-oxidizing catalyst which has superior activity and selectivity in carrying out a reaction for partially oxidizing hydrocarbon in the presence of hydrogen and oxygen.

The second partially-oxidizing catalyst for hydrocarbon (hereinafter, referred to simply as catalyst (2)) contains gold, a metal oxide containing titanium, and at least one element selected from the group consisting of an alkaline metal, an alkaline-earth metal and thallium.

With respect to the above-mentioned gold, particles having a particle-diameter of not more than 10 nanometer (nm), that is, so-called ultrafine particles, are preferably used. Further, it is preferable for the gold to be deposited onto a metal oxide containing titanium.

The carrier amount (content) of gold in catalyst (2) is preferably set at not less than 0.001% by weight, more preferably set in the range of 0.005% to 5% by weight, most preferably set in the range of 0.01% to 1% by weight, and by far the most preferably set in the range of 0.02% to 0.5% by weight. A carrier amount of gold below 0.001% by weight is not preferable because it causes degradation in the activity of catalyst (2). Further, a carrier amount of gold exceeding 5% by weight is not preferable because no further improvements in the activity of catalyst (2) is obtained as compared with the case in which gold is deposited within the above-mentioned range and because gold is wastefully used.

The above-mentioned metal oxide containing titanium is not particularly limited, as long as it is a metal oxide containing titanium. In other words, any metal oxide containing titanium may be adopted as long as it contains titania (that is, titanium dioxide: $TiO_2$) and/or a complex oxide containing titanium (hereinafter, referred to as a titanium-containing complex oxide); and if necessary, it may contain a metal oxide containing no titanium, such as alumina and silica.

Although not particularly limited, titania having a crystal structure of the amorphous or anatase-type is preferably used as the above-mentioned titania. Further, with respect to the above-mentioned titanium-containing complex oxide, for example, the following materials are listed: a complex oxide between titanium and other metals, such as titaniazirconia, $FeTiO_3$, $CaTiO_3$, $SrTiO_3$; a zeolitic compound in which titanium such as titano-silicate is combined inside the zeolite lattice; etc. The shape of the titania and titanium-containing complex oxide is not particularly limited; and it may formed into powder or various shapes.

Further, in order to improve the activity of catalyst (2), the above-mentioned titania and/or titanium-containing complex oxide is preferably used in a state in which it is deposited (fixed) on a carrier (support).

With respect to the carrier, carriers, which are made of metal oxides and various metals and which contain no titanium, may be used. More specifically, for example, the following materials are used as the carrier: alumina (aluminum oxide), silica (silicon dioxide: $SiO_2$), magnesia (magnesium oxide: MgO), cordierite, zirconium oxide, and ceramics made of complex oxides, etc. of these materials; crystalline metallosilicates such as zeolite; foamed materials made of various metals; honeycomb carriers made of various metals; pellets made of various metals; etc.

It is preferable for the carrier to contain alumina and/or silica, and it is more preferable to contain silica. Here, the expression "containing alumina and silica" is defined as including cases containing zeolite (alumino-silicate) and silica alumina.

The crystal structure, shape, size, etc. of the carrier are not particularly limited; however, it is preferable to set its specific surface area of the carrier at not less than 50 $m^2/g$, and more preferably at not less than 100 $m^2/g$. By setting the specific surface area at not less than 50 $m^2/g$, the performance of catalyst (1) is further improved. In other words, since side reactions, such as serial oxidation, are further suppressed, it is possible to partially oxidizing hydrocarbon more effectively. Additionally, titanium or a titanium-containing complex oxide may be deposited on the carrier through a calcination process after a titanium compound such as a complex has been deposited on a carrier.

The content of titanium in catalyst (2), upon conversion to $TiO_2$, is preferably set in the range of 0.1% to 20% by weight, and more preferably set in the range of 0.5% to 10% by weight. A titanium content of less than 0.1% by weight (upon conversion to $TiO_2$) is not preferable since the activity of catalyst (2) decreases. Further, a titanium content exceeding 20% by weight (upon conversion to $TiO_2$) is not preferable because no further improvements in the activity of catalyst (2) are obtained as compared with the case in which titanium in the above-mentioned range, is contained.

In addition to the above-mentioned gold and titanium-containing metal oxide, catalyst (2) of the present invention contains at least one element selected from the group consisting of an alkaline metal, an alkaline-earth metal and thallium. With respect to the alkaline metal, Li, Na, K, Rb, Cs and Fr may be adopted. With respect to the alkaline-earth metal, Be, Mg, Ca, Sr, Ba and Ra may be adopted.

With respect to the above-mentioned elements, at least one element selected from the group consisting of K, Rb and Cs and at least one element selected from the group consisting of Mg, Ca, Sr and Ba are more preferably adopted. Thus, it becomes possible to further improve the performance of catalyst (2). In other words, since side reactions, such as serial oxidation, are further suppressed, it is possible to partially oxidizing hydrocarbon more effectively.

In catalyst (2), the above-mentioned element may exist as a simple metal element or it may be incorporated into another component, for example, the crystalline structure of the titanium-containing metal oxide. Further, the abovementioned mentioned element may be contained in the aforementioned carrier (support); however, in this case, effects as described above are not expected. Therefore, in the case when the carrier (support) is used in a separate manner, the amount of the above-mentioned element contained in the carrier (support) (for example, Mg which is an alkaline-earth metal in a magnesia carrier) is excluded from the definition of the content by which the effects are obtained.

In catalyst (2), the content of at least one element selected from the group consisting of an alkaline metal, an alkaline-earth metal and thallium (hereinafter, referred to as a specific element) is preferably set in the range of 0.001% to 20% by weight, more preferably set in the range of 0.005% to 5% by weight, and most preferably set in the range of 0.01% to 2% by weight as a simple metal with respect to the entire weight of catalyst (2). Here, the specific element, when contained in the carrier that is applied in a separate manner, is excluded from the definition of the content.

A carrier amount of specific element of less than 0.001% by weight is not preferable since the effect of addition of the specific element no longer appears. Further, a carrier amount of specific element exceeding 20% by weight is not preferable since the effect of addition of the specific element is no longer recognized as compared with the case in which the specific element in the above-mentioned ranged is applied and since degradation in the performance of catalyst (2) is raised.

Next, an explanation will be given of a preparing method for catalyst (2).

The preparing method for catalyst (2) is not particularly limited, as long as it is a preparing method for forming a composition containing gold, a titanium-containing metal oxide, and at least one element selected from the group consisting of an alkaline metal, an alkaline-earth metal and thallium.

With respect to the preparing method for catalyst (2), the following methods are listed, although the present invention is not intended to be limited thereby: a method in which after preparing a catalyst made of ultrafine gold particles and a titanium-containing metal oxide by allowing the ultrafine gold particles to be deposited on the titanium-containing metal oxide (hereinafter, referred to as a ultrafine-gold-particle-titanium-containing-metal-oxide catalyst), at least one element selected from the group consisting of an alkaline metal, an alkaline-earth metal, and thallium is deposited on the ultrafine-gold-particle-titanium-containing-metal-oxide catalyst; another method in which after allowing the specific element to be deposited on a titanium-containing metal oxide, ultrafine gold particles are deposited on the titanium-containing metal oxide; and the other method in which ultrafine gold particles are deposited on a titanium-containing metal oxide while the specific element is deposited thereon at the same time.

With respect to the preparing methods for catalyst (2), the second and third methods among the above-mentioned examples are preferably adopted: that is, the methods, in which before gold is allowed to deposit on the titanium-containing containing metal oxide, or simultaneously as gold is allowed to deposit on the titanium-containing metal oxide, at least one element selected from the group consisting of an alkaline metal, an alkaline-earth metal and thallium is allowed to deposit on the titanium-containing metal oxide, are preferably adopted.

In the first method in which after preparing a ultrafine-gold-particle-titanium-containing-metal-oxide catalyst by allowing the ultrafine gold particles to be deposited on the titanium-containing metal oxide, the specific element is added, with respect to the method for allowing the ultrafine gold particles to deposit on the titanium-containing metal oxide, for example, the deposition-precipitation method, the coprecipitation method, the impregnation method, the chemical vapor deposition method and other methods, which use gold or a gold compound, are listed; however, the present invention is not particularly limited thereby.

With respect to the method for preparing a ultrafine-gold-particle-titanium-containing-metal-oxide catalyst by allowing ultrafine gold particles to deposit on the titanium-containing metal oxide, the following specific examples are listed: a method in which after allowing titania and/or a titanium-containing complex oxide to deposit on a carrier, the carrier is immersed into an aqueous solution containing a gold compound so that gold deposit is precipitated on the carrier; and another method in which a carrier made of titania and/or a titanium-containing complex oxide is immersed into an aqueous solution containing a gold compound so that gold deposit is precipitated on the carrier. With these deposition methods, the ultrafine gold particles are firmly fixed onto the carrier with a comparatively uniform distribution. In the case when ultrafine gold particles and a titanium oxide are deposited on the carrier in a separate manner, it is preferable to deposit gold after depositing the titanium oxide.

With respect to methods for depositing titania and/or a titanium-containing complex oxide onto a carrier such as silica and alumina, the deposition-precipitation method, the coprecipitation method, the impregnation method and other methods are listed; or the deposition can be carried out by coating or by dispersing it to form a so-called island structure.

The above-mentioned gold compound is not particularly limited, as long as it is water soluble; and for example, chloroauric acid may be adopted. The temperature of the aqueous solution is preferably set in the range of 30° C. to 80° C., although it is not particularly limited. In this case, the pH of the aqueous solution may be adjusted in the range of 6 to 10, if necessary, and in order to increase the carrier amount of gold in catalyst (2) or in order to reduce the particle diameter of ultrafine gold particles, a surface active agent, carbonate and/or a salt thereof may be added to the aqueous solution.

More specifically, with respect to the surface active agent, a long-chain alkyl (aryl) sulfonic acid whose carbon number is not less than 8 and a salt thereof, and a long-chain alkyl (aryl) carbonate and a salt thereof are adopted. Here, with respect to the carbonate and a salt thereof, for example, citric acid and its sodium salt and magnesium salt are adopted.

In the above-mentioned first method, with respect to methods for adding the specific element to the ultrafine-gold-particle-titanium-containing-metal-oxide catalyst, conventional commonly-used methods, such as the impregnation method, may be adopted. More specifically, in the case of the impregnation method, for example, the ultrafine-gold-particle-titanium-containing-metal-oxide catalyst in powdered form or a molded form is immersed into an aqueous solution containing the specific element, that is, an aqueous solution of a carbonate of alkaline-metal such as potassium carbonate, cesium carbonate and rubidium carbonate, and the specific element can be forcefully deposited onto the ultrafine-gold-particle-titanium-containing-metal-oxide by distilling and removing water.

With respect to the second method in which after adding the specific element to a titanium-containing metal oxide, ultrafine gold particles are deposited onto the titanium-containing metal oxide, for example, onto the titanium-containing metal oxide containing the specific element that is obtained by a method such as impregnating the specific element into the titanium-containing metal oxide, the ultrafine gold particles may be deposited by a method, such as the deposition-precipitation method, the coprecipitation method, the impregnation method and the chemical vapor deposition method, by using gold or a gold compound.

Here, with respect to methods for obtaining the titanium-containing metal oxide containing the specific element by impregnating the specific element into the titanium-containing metal oxide, for example, the following and other methods may be adopted; that is, the titanium-containing oxide in powdered form or a molded form is immersed into an aqueous solution containing the specific element, for example, an aqueous solution of an alkaline-metal carbonate salt, and water is distilled and removed.

Moreover, the titanium-containing metal oxide containing the specific element may also be obtained by a method in which the titanium and/or a titanium-containing complex oxide and an oxide containing the specific element, that is, for example, an oxide of an alkaline-earth metal such as magnesium oxide, are simultaneously deposited onto a carrier such as silica.

With respect to the third method in which the specific element is added simultaneously as ultrafine gold particles are deposited onto the titanium containing metal oxide, for example, the following and other method may be adopted; that is, when gold is deposited on the titanium-containing metal oxide by the deposition-precipitation method in which the titanium-containing metal oxide is added after the pH of an aqueous solution of a gold compound has been adjusted by a neutralizer, an aqueous solution containing the specific element (for example, an aqueous solution of an alkaline-metal hydroxide such as cesium hydroxide) is used as the neutralizer for adjusting the pH.

As described above, the second partially-oxidizing catalyst for hydrocarbon of the present invention contains at least one element selected from the group consisting of gold, a titanium-containing metal oxide, an alkaline metal, an alkaline-earth metal and thallium.

In the above-mentioned composition, it is possible to provide a partially-oxidizing catalyst having superior activity and selectivity in carrying out a reaction for partially oxidizing hydrocarbon in the presence of hydrogen and oxygen. Therefore, the second partially-oxidizing catalyst is preferably used as a catalyst for manufacturing epoxides by partially oxidizing hydrocarbon of the olefin family or as a catalyst for manufacturing alcohols and/or ketones by partially oxidizing saturated hydrocarbon.

The partially-oxidizing method for hydrocarbon of the present invention is a method for partially oxidizing hydrocarbon in the presence of oxygen and hydrogen by the use of catalyst (1) or catalyst (2). In the above-mentioned partially-oxidizing method, with respect to hydrocarbon used as a raw material, a saturated hydrocarbon and a unsaturated hydrocarbon, such as hydrocarbons of the olefin family, are listed.

With this method, since a hydrocarbon of the olefin family is used as the hydrocarbon, the double bond of the hydrocarbon of the olefin family (unsaturated hydrocarbon) is selectively oxidized so that an epoxide is selectively manufactured. Further, since a saturated hydrocarbon is used as the hydrocarbon, the secondary carbon-hydrogen bond as well as the tertiary carbon-hydrogen bond is selectively oxidized. In other words, in the above-mentioned partially oxidizing reaction, the order of reactivity in the carbon-hydrogen bonds of the saturated hydrocarbon is represented by: tertiary carbon>secondary carbon>primary carbon; and the primary carbon-hydrogen bond is hardly oxidized. When the secondary carbon-hydrogen bond is oxidized, a ketone is mainly manufactured, and when the tertiary carbon-hydrogen bond is oxidized, an alcohol is mainly manufactured.

The above-mentioned saturated hydrocarbon is not particularly limited; however, those compounds whose carbon number is in the range of 3 to 12 are preferably adopted. More specifically, the following saturated hydrocarbons are, for example, listed: propane, n-butane, isobutane, cyclobutane, n-pentane, 2-methylbutane, cyclopentane, n-hexane, 2-methylpentane, 3-methylpentane, cyclohexane, 2-ethylhexane and n-octane.

The above-mentioned hydrocarbon of the olefin family (unsaturated hydrocarbon) is not particularly limited, as long as it is a compound having the olefin double bond; however, those compounds whose carbon number is in the range of 2 to 12 are preferably adopted. More specifically, the following hydrocarbons of the olefin family are, for example, listed: terminal olefines, such as ethylene, propylene, 1-butene, isobutylene, 1-pentene, 2-methyl-1-butene, 3-methyl-1-butene, 1-hexene, 2-methyl-1-pentene, 3-methyl-1-pentene, 4-methyl-1-pentene, styrene and α-methylstyrene; internal olefines, such as 2-butene, 2-pentene, cyclopentene, 2-hexene, 3-hexene, cyclohexene, 1-methyl-1-cyclopentene and 3-methyl-1-cyclopentene; and dienes such as 1-3-butadiene.

In the partially-oxidizing method of the present invention, the following corresponding epoxides are manufactured by adopting the hydrocarbons of the olefin family as exemplified above as the hydrocarbon to be used therein: ethyleneoxide, propyleneoxide, 1,2-epoxybutane, 2-methyl-1,2-epoxypropane, 1,2-epoxypentane, 2-methyl-1,2-epoxybutane, 3-methyl-1,2-epoxybutane, 1,2-epoxyhexane, 2-methyl-1,2-epoxypentane, 3-methyl-1,2-epoxypentane, 4-methyl-1,2-epoxypentane, (1,2-epoxyethyl) benzene (that is, styrene oxide), (1-methyl-1,2-epoxyethyl) benzene; 2,3-epoxybutane, 2,3-epoxypentane, 1,2-epoxycyclopentane (that is, cyclopentene oxide), 2,3-epoxyhexane, 3,4-epoxyhexane, 1,2-epoxycyclohexane (that is, cyclohexene oxide), 1-methyl-1,2-epoxycyclopentane, 3-methyl-1,2-epoxycyclopentane; 3,4-epoxy-1-butene.

The reaction for partially oxidizing a hydrocarbon of the present invention is preferably carried out in a gaseous phase, although it may be carried out in a liquid phase. The following description will exemplify cases in which the reaction is carried out in a gaseous phase.

Although not particularly limited as long as it is set in accordance with the content of gold and titanium, the carrier amount of titanium oxide, the kind of hydrocarbon, the reaction conditions, etc., the amount of use of the catalyst (catalyst (1) or catalyst (2)) is preferably set so that the space velocity (SV) of the hydrocarbon during the reaction is maintained in the range of 100 $hr^{-1}$·ml/g·cat. to 10,000 $hr^{-1}$·ml/g·cat. (space velocity per 1 gram of catalyst).

Hydrogen (molecular hydrogen) reacts as a reducing agent. Although not particularly limited, the amount of use of hydrogen is preferably set at such an amount that the volume ratio of hydrogen and hydrocarbon (hydrogen/hydrocarbon) is maintained in the range of 1/10 to 100/1. Here, the greater the ratio of hydrogen, the greater the reaction rate; therefore, the closer to 100/1 the volume ratio is set, the more preferable it becomes. Additionally, in the absence of hydrogen, the hydrocarbon is completely oxidized to become carbon dioxide and water. In this case, it is not possible to obtain an alcohol and a ketone, or an epoxide.

The reaction of the present invention for partially oxidizing a hydrocarbon is carried out by allowing a material gas containing the hydrocarbon, oxygen (molecular oxygen) and hydrogen to contact catalyst (1) or catalyst (2). Therefore, with respect to the reaction method, for example, a method in which catalyst (1) or catalyst (2) is loaded in a reaction device and the material gas is passed through the reaction device is preferably adopted. Thus, it is possible to obtain a resulting gas containing an alcohol and/or a ketone or an epoxide (hereinafter, referred to as object.)

Additionally, although the reaction method is not particularly limited, the above-mentioned reaction is a so-called catalyst reaction in an ununiform gaseous phase; therefore, a continuous method is preferably adopted. Moreover, the material gas may contain an inactive gas, such as nitrogen, helium, argon and carbondioxide, if necessary. In other words, the hydrocarbon may be diluted by an inactive gas, if necessary.

The reaction temperature is not particularly limited, and is properly set in accordance with the kind, etc. of the hydrocarbon; however, it is preferably set, for example, in the range of 0° C. to 300° C. in which the hydrocarbon or the object can exist as gases, and is more preferably set in the range of 100° C. to 250° C. In the case when the reaction temperature is extremely high, the burning reaction of the hydrocarbon and object easily takes place, that is, the production of carbondioxide and water easily takes place, resulting in an increase in the amount of hydrogen to be burned. Therefore, it becomes difficult to manufacture the object effectively. However, since the partially oxidizing reaction also progresses effectively with the reaction temperature maintained relatively high, it is preferable to set the reaction temperature at not less than 100° C. in the present invention. In the present invention, the burning reaction of the hydrocarbon and the object can be suppressed even at high temperatures not less than 100° C.

Moreover, the reaction pressure is not particularly limited, and is properly set in accordance with the reaction conditions such as the reaction temperature; however, it is preferably set at a pressure in which the hydrocarbon and object exist as gases, for example, in the range of 0.05 MPa to 5 MPa. The reaction time is not particularly limited, and is properly set in accordance with the reaction conditions, such as the reaction temperature and reaction pressure.

Additionally, in the case when the reaction for partially oxidizing a hydrocarbon in a liquid phase, the reaction temperature is preferably set at a temperature in which the hydrocarbon and object exist as liquids, for example, in the range of 0° C. to 100° C. Further, the reaction pressure is set at a pressure in which the hydrocarbon and the object exist as liquids.

Alternatively, the above-mentioned reaction may be carried out in a liquid phase by using an inactive solvent to the reaction. With respect to such a reaction method using a solvent, for example, a method in which the above-mentioned material gas is bubbled in a suspension that is prepared by suspending the solvent in catalyst (1) or catalyst (2) is preferably adopted. With respect to the solvent, for example, an aromatic hydrocarbon such as benzene and a halogenated hydrocarbon such as methylene chloride are listed; however, the present invention is not particularly limited thereby.

As described above, the partially-oxidizing method for a hydrocarbon of the present invention is a method in which the hydrocarbon is partially oxidized in the presence of oxygen and hydrogen by using catalyst (1) or catalyst (2).

In the case of the application of catalyst (1) in the above-mentioned method, it is possible to partially oxidizing the hydrocarbon simply as well as effectively by synergistic effects of gold, titanium oxide and the carrier, that is, by the specific, synergistic effects demonstrated by these components.

In this manner, the application of a direct oxidation in a gaseous phase, that is, an oxidizing reaction in a gaseous phase, makes it possible to reduce the number of reaction processes to one reaction process (one stage), and it is possible to obtain an alcohol and/or a ketone from a saturated hydrocarbon with high selectivity and high conversion, and also to obtain an epoxide from a unsaturated hydrocarbon with high selectivity and high conversion, as well as reducing the amount of hydrogen to be burned.

In the case of the application of catalyst (2) in the above-mentioned method, it is possible to partially oxidizing the hydrocarbon simply as well as effectively by synergistic effects of gold, a titanium-containing metal oxide and at least one element selected from the group consisting of an alkaline metal, an alkaline-earth metal and thallium that are contained in catalyst (2). With this arrangement, it is possible to obtain an epoxide from a hydrocarbon of the olefin family and also to obtain an alcohol and/or a ketone from a saturated hydrocarbon respectively with high selectivity and high conversion merely by using one process (one stage).

The effect of the addition of at least the one element selected from the group consisting of an alkaline metal, an alkaline-earth metal and thallium that are contained in catalyst (2) is particularly demonstrated to improve the activity in producing the epoxide and also to improve the selectivity of the epoxide.

The principle of the function of the specific element has not been clarified yet; however, it has been found that when an epoxidizing reaction of a hydrocarbon of the olefin family is carried out by using a catalyst to which no specific element is added, the ratio of production of compounds such as aldehydes and ketones, which appear to be produced through isomerization of the epoxide, tends to increase and the conversion of hydrogen also tends to increase. Therefore, it is considered that the principle of the function of the specific element is based on the fact that the strong-acid point of the carrier is poisoned by the addition of the specific element that is basic so that sequential side reactions, such as the isomerization of the epoxide, are suppressed or the fact that the reactivity of hydrogen is improved by the change in physical property of the catalyst surface by the presence of the specific element. Here, in general, the fact that the isomerization reaction of an epoxide is accelerated by a strong acid has been well known.

In addition, another effect of the addition of the specific element is that it improves the stability in life time of the catalyst. In other words, the addition of the specific element makes it possible to suppress the production of side products, thereby suppressing accumulation of resin-state matters on the surface of the catalyst, which appears to be caused by the side products; consequently, this provides a secondary effect, that is, suppression of degradation with time of the catalyst.

For a fuller understanding of the nature and advantages of the invention, reference should be made to the ensuing detailed description.

THE BEST MODE FOR CARRYING OUT THE INVENTION

The following description will discuss the present invention in more detail by reference to examples and comparative examples; however, the present invention is not particularly limited thereby.

EXAMPLE 1

In 500 ml of a methyl alcohol solution containing 1.96 g of titanylacetylacetonate, 60 g of silicon oxide serving as a carrier (Brand Name: CARIACT Q-10, manufactured by Fujisilysia Chemical, Ltd.; specific surface area 326 m$^2$/g; 10 mesh to 20 mesh; 840 μm to 1,700 μm in particle diameter) was immersed, and then the methyl alcohol was distilled and removed by using an evaporator. The resultant solid matter was dried at 120° C. for 12 hours, and then calcined at 600° C. in the air for three hours so that a silicon oxide having titanium oxide deposited thereon was obtained. The carrier amount of the titanium oxide was 1% by weight.

Next, 0.344 g of tetrachloroauric (III) acid was dissolved in water, and by adjusting it to pH 8.8 by using a sodium hydroxide solution, 500 ml of an aqueous solution of tetrachloroauric (III) acid was prepared. To this aqueous solution, 10 g of the silicon oxide having titanium oxide deposited thereon was added at 70° C., and stirred for one hour so as to suspend the silicon oxide having titanium oxide deposited thereon (titania-silica), and gold deposition was immobilized on the surface thereof.

Thereafter, the suspension was filtered, and the remaining matter, thus filtered, was washed by water and dried. Then, the remaining matter was calcined at 400° C. in the air for three hours so that a gold-titania-silica catalyst, which is a catalyst consisting of titinia-silica having gold particles deposited thereon, was obtained as a partially-oxidizing catalyst.

Meanwhile, the content of gold in the filtrated solution and the washing liquid, that is, the amount of gold that had not been deposited, was measured by the induction-coupling high-frequency plasma spectral analysis (ICP). Thus, the carrier amount of gold deposited on the silicon oxide having titanium oxide deposited thereon was calculated by subtracting the amount of gold that had been obtained through the measurements from the amount of gold in the tetrachloroauric (III) acid that had been prepared. As a result, the carrier amount of gold in the gold-titania-silica catalyst was 0.37% by weight.

Next, the performance of the silicon oxide which had titanium oxide deposited thereon and onto which gold was deposited was examined with respect to a partially-oxidizing reaction for propylene that serves as a hydrocarbon (an unsaturated hydrocarbon). In other words, 1.0 g of the gold-titania-silica catalyst thus obtained was loaded into a stainless reaction cell (reaction device) with an 8 mm inside diameter. Meanwhile, a material gas was prepared by mixing propylene, hydrogen, oxygen and argon so as to have a volumetric ratio of 10/10/10/70 (propylene/hydrogen/oxygen/argon). After the layer of the silicon oxide which had titanium oxide deposited thereon and onto which gold was deposited had been heated to a temperature of 150° C., the material gas, which had been pressurized to 3 atmospheric pressure, was passed through the reaction cell at a flow rate of 5,000 ml/hr (standard state) so as to allow propylene to react at 150° C.

Thirty minutes after the start of the reaction, the resultant production gas was sampled at the exit of the reaction cell, and the composition was analyzed by gas chromatography (GC). As a result, the conversion of propylene was 6.8%, the selectivity to propyleneoxide, which is an epoxide, was 91.0%, and the conversion of hydrogen was 36.4%. The results showed that the space time yield of propyleneoxide was 80.2 g/hr/kg·cat (the space time yield per 1 kg of the catalyst) and 21.7 g/hr/g·Au (the space time yield per 1 g of Au).

EXAMPLE 2

In 500 ml of a methyl alcohol solution containing 5.12 g of titanium (IV) tetrabutoxide and 4.51 g of 2,4-pentanedione, 60 g of silicon oxide serving as a carrier (Brand Name: CARIACT Q-15, manufactured by Fujisilysia Chemical, Ltd.; specific surface area 196 m²/g; 10 mesh to 20 mesh; 840 μm to 1,700 μm in particle diameter) was immersed, and then the methyl alcohol was distilled and removed by using an evaporator. The resultant solid matter was dried at 120° C. for 12 hours, and then calcined at 600° C. in the air for three hours so that a silicon oxide having titanium oxide deposited thereon (titania-silica) was obtained. The carrier amount of the titanium oxide was 2% by weight.

Next, 0.172 g of tetrachloroauric (III) acid was dissolved in water, and by adjusting it to pH 8.5 by using a sodium hydroxide solution, 500 ml of an aqueous solution of tetrachloroauric (III) acid was prepared. To this aqueous solution, 10 g of the silicon oxide having titanium oxide deposited thereon was added at 70° C., and stirred for one hour so as to suspend the silicon oxide which had titanium oxide deposited thereon and onto which gold deposition was immobilized.

Thereafter, the suspension was filtered, and the remaining matter through filtration was washed by water and dried. Then, the remaining matter through filtration was calcined at 300° C. in the air for three hour so that a gold-titinia-silica catalyst, which is a catalyst consisting of titinia-silica having gold particles deposited thereon, was obtained as a partially-oxidizing catalyst.

Then, the carrier amount of gold deposited on the silicon oxide having titanium oxide deposited thereon was calculated in the same manner as Example 1. As a result, the carrier amount of gold was 0.22% by weight.

Next, the performance of the gold-titania-silica catalyst was examined with respect to a partially-oxidizing reaction for propylene by using the same reactions, analyses, etc. as those of Example 1. As a result, the conversion of propylene was 5.4%, the selectivity to propylene oxide was 93.2%, and the conversion of hydrogen was 23.3%. The results showed that the space time yield of propyleneoxide was 65.2 g/hr/kg·cat (the space time yield per 1 kg of the catalyst) and 29.6 g/hr/g·Au (the space time yield per 1 g of Au).

Comparative Example 1

0.172 g of tetrachloroauric (III) acid was dissolved in water, and by adjusting it to pH 8.8 by using a sodium hydroxide solution, 2,000 ml of an aqueous solution of tetrachloroauric (III) acid was prepared. To this aqueous solution, 20 g of titanium oxide (Brand Name: titania P-25, manufactured by Japan Aerosil Ltd.) was added, and stirred for one hour so as to suspend the titanium oxide, while gold deposition was immobilized on the surface thereof.

Thereafter, the suspension was filtered, and the remaining matter through filtration was washed by water and dried. Then, the remaining matter was molded by a pellet-molding device into pillar-shaped mold product in 1 mm φ×2 mm. The resulting mold product was dried at 120° C. for 12 hours, and then was calcined at 400° C. in the air for three hour so that a titanium oxide having gold deposited thereon that was to be used for comparative purpose was prepared.

In other words, the titanium oxide having gold deposited thereon was prepared without using silicon oxide or aluminum oxide as a carrier. The carrier amount of gold deposited on the comparative gold-titania catalyst was calculated in the same manner as Example 1. As a result, the carrier amount of gold was 0.49% by weight.

Next, the performance of the comparative gold-titania catalyst was examined with respect to a partially-oxidizing reaction for propylene by using the same reactions, analyses, etc. as those of Example 1. With respect to the comparative catalyst (gold-titania catalyst), in order to examine whether its catalyst performance is improved as temperature increases, reactions were implemented by using the same operations as those of Example 1 respectively at three points of reaction temperature, 80° C., 120° C. and 150° C.

As a result, in the case of the reaction temperature of 80° C., the conversion of propylene was 1.2%, the selectivity to propylene oxide was 89.5%, and the conversion of hydrogen was 12.7%. The results showed that the space time yield of propyleneoxide was 13.9 g/hr/kg·cat.

In the case of the reaction temperature of 120° C., the conversion of propylene was 1.8%, the selectivity to propylene oxide was 53.1%, and the conversion of hydrogen was 29.3%. The results showed that the space time yield of propyleneoxide was 12.4 g/hr/kg·cat and 2.5 g/hr/g·Au (the space time yield per 1 g of Au).

Further, in the case of the reaction temperature of 150° C., the conversion of propylene was 2.4%, the selectivity to propylene oxide was 38.6%, and the conversion of hydrogen was 44.1%. The results showed that the space time yield of propyleneoxide was 12.0 g/hr/kg·cat.

As described above, when used at high reaction temperatures such as not less than 100° C., the comparative catalyst is extremely susceptible to degradation in the selectivity to propylene oxide although the conversions of propylene and hydrogen improve, thereby resulting a reduction in the yield of propyleneoxide.

EXAMPLE 3

Reactions, analyses, etc. were implemented in the same manner as those of Example 1, except that the volumetric ratio of the material gas (propylene/hydrogen/oxygen/argon) was changed to 5/10/10/75, the pressure of the material gas (reaction pressure) was set normal and the reaction temperature was changed to 180° C. in the partially-oxidizing reaction for propylene in Example 1. As a result, the conversion of propylene was 8.5%, the selectivity to propylene oxide was 78.1%, and the conversion of hydrogen was 43.3%. The results showed that the space time yield of propyleneoxide was 43.1 g/hr/kg·cat.

EXAMPLE 4

Reactions, analyses, etc. were implemented in the same manner as those of Example 2, except that the reaction temperature was changed from 150° C. to 180° C. in the partially-oxidizing reaction for propylene in Example 2. As a result, the conversion of propylene was 8.3%, the selectivity to propylene oxide was 71.1%, and the conversion of hydrogen was 62.0%. The results showed that the space time yield of propyleneoxide was 76.5 g/hr/kg·cat.

EXAMPLE 5

Reactions, analyses, etc. were implemented in the same manner as those of Example 2, except that the flow rate of the material gas was changed from 5,000 ml/hr to 8,000 ml/hr (normal pressure state) in the partially-oxidizing reaction for propylene in Example 2. As a result, the conversion of propylene was 3.4%, the selectivity to propylene oxide was 93.0%, and the conversion of hydrogen was 15.5%. The results showed that the space time yield of propyleneoxide was 66.3 g/hr/kg·cat.

EXAMPLE 6

First, the same processes as those of Example 1 were implemented, except that the calcination temperature was changed from 600° C. to 800° C., so that a silicon oxide having titanium oxide deposited thereon (the carrier amount of titanium oxide: 1% by weight) was obtained.

Next, 900 ml of an aqueous solution containing 0.34 g of chloroauric acid was heated to 70° C., and adjusted to pH 8.9 by using a potassium hydroxide solution. Then, while stirring this aqueous solution, 20 g of the silicon oxide having titanium oxide deposited thereon (titania-silica) was added, and the solution was stirred at 70° C. for one hour.

Next, supernatant liquid was removed from the aqueous solution containing solid matter, and the resultant solid matter was washed three times by 1,000 ml of water, and then filtered. Thereafter, the solid matter thus filtered was dried at 120° C. for 12 hours, and then calcined at 400° C. in the air for three hours so that a gold-titania-silica catalyst, which is a catalyst consisting of titania-silica having ultrafine gold particles deposited thereon, was obtained. The content of gold contained in the gold-titania-silica catalyst, when analyzed by the fluorescence X-ray spectroscopy, was 0.052% by weight.

Next, propylene, which serves as an saturated hydrocarbon, was partially oxidized by using the gold-titania-silica catalyst. In other words, 4 g of the gold-titania-silica catalyst was loaded into a stainless reaction vessel with an 8 mm inside diameter. Next, in a state in which the temperature of the catalyst layer was heated to 165° C. under three atmospheric pressure, a mixed gas consisting of hydrogen, oxygen, propylene and argon with a volumetric ratio of 20/10/10/60 (hydrogen/oxygen/propylene/argon) was passed through the reaction vessel at a flow rate of 16,000 ml/hr so as to carry out reaction.

Fifteen minutes after the start of the reaction, the resultant production gas was sampled at the exit of the reaction cell, and the composition was analyzed by gas chromatography (GC). As a result, the yield of propyleneoxide, which is a corresponding epoxide, was 9.6%, and the conversion of hydrogen was 13.6% and the space time yield of propyleneoxide was 90.7 g/hr/kg·cat.

EXAMPLE 7

First, the same processes as those of Example 1 were implemented, except that the amount of titanium oxide (II) acetylacetonate was changed from 1.96 g to 5.88 g, so that a silicon oxide having titanium oxide deposited thereon with a carrier amount of titanium oxide of 3% by weight was obtained.

Thereafter, gold was deposited on the silicon oxide having titanium oxide deposited thereon by the same processing method as that of Example 6 so that a gold-titania-silica catalyst was obtained. The content of gold contained in the gold-titania-silica catalyst, when analyzed by the fluorescence X-ray spectroscopy, was 0.068% by weight.

Next, propylene, which serves as an un-saturated hydrocarbon, was partially oxidized by using the gold-titania-silica catalyst. In other words, 2 g of the gold-titania-silica catalyst was loaded into a stainless reaction vessel with an 8 mm inside diameter. Next, in a state in which the temperature of the catalyst layer was heated to 165° C. under three atmospheric pressure, a mixed gas consisting of hydrogen, oxygen, propylene and argon with a volumetric ratio of 40/10/10/40 (hydrogen/oxygen/propylene/argon) was passed through the reaction vessel at a flow rate of 8,000 ml/hr so as to carry out reaction.

Fifteen minutes after the start of the reaction, the resultant production gas was sampled at the exit of the reaction vessel, and the composition was analyzed by gas chromatography. As a result, the yield of propyleneoxide, which is a corresponding epoxide, was 6.9%, and the conversion of hydrogen was 5.9% and the space time yield of propyleneoxide was 65.9 g/hr/kg·cat.

EXAMPLE 8

In 500 ml of a methyl alcohol solution containing 1.96 g of titanium oxide (II) acetylacetonate, 60 g of silica serving as a carrier (Brand Name: Silica ID gel, manufactured by Fuji Davison Chemical Co., Ltd.; specific surface area 291 m$^2$/g; 20 mesh to 40 mesh) was immersed, and then the methyl alcohol was distilled and removed by using an evaporator. The resultant solid matter was dried at 120° C. for 12 hours, and then calcined at 600° C. in the air for three hours so that a silica having titanium oxide deposited thereon was obtained. With respect to the carrier, the carrier amount of the titanium oxide was 1% by weight.

Next, 0.172 g of tetrachloroauric (III) acid was dissolved in water, and by adjusting it to pH 8.7 by using a sodium hydroxide solution, 500 ml of an aqueous solution of tetrachloroauric (III) acid was prepared. To this aqueous solution, 10 g of the silica having titanium oxide deposited thereon was added at 70° C., and stirred for one hour so as to suspend the silica having titanium oxide deposited thereon (titania-silica), and gold deposition was immobilized on the surface thereof.

Thereafter, the suspension was filtered, and the remaining matter through filtration was washed by water and dried. Then, the remaining matter through filtration was calcined at 400° C. in the air for three hour so that a gold-titania-silica catalyst, which is a catalyst consisting of titinia-silica having gold particles deposited thereon, was obtained as a partially-oxidizing catalyst.

Next, the performance of the silica which had titanium oxide deposited thereon and onto which gold was deposited was examined with respect to a partially-oxidizing reaction for propane that serves as a hydrocarbon (a saturated hydrocarbon). In other words, 1.0 g of the silica which had titanium oxide deposited thereon and onto which gold was deposited thus obtained was loaded into a stainless reaction cell (reaction device) with an 8 mm inside diameter. Meanwhile, a material gas was prepared by mixing propane, hydrogen, oxygen and argon so as to have a volumetric ratio of 5/40/10/45 (propane/hydrogen/oxygen/argon). After the layer of the gold-titania-silica catalyst had been heated to a temperature of 120° C., the material gas was passed through the reaction cell at a flow rate of 2,000 ml/hr (standard state) under normal pressure, so as to allow propane to react at 120° C.

Thirty minutes after the start of the reaction, the resultant production gas was sampled at the exit of the reaction cell, and the composition was analyzed by gas chromatography. As a result, the conversion of propane was 0.48%, and the selectivity to acetone, which is a ketone, was 58.8%. The results showed that the space time yield of propane to acetone was 1.5 g/hr/kg·cat.

EXAMPLE 9

Reactions, analyses, etc. were implemented in the same manner as those of Example 8, except that isobutane was used as a hydrocarbon (a saturated hydrocarbon) in place of propane in the partially-oxidizing reaction for hydrocarbon in Example 8. As a result, the conversion of isobutane was 1.04%, the selectivity to t-butyl alcohol which is an alcohol was 84.8%, and the selectivity to acetone which is a ketone was 7.7%. The results showed that the space time yield of isobutane to t-butyl alcohol was 5.8 g/hr/kg·cat.

Comparative Example 2

0.172 g of tetrachloroauric (III) acid was dissolved in water, and by adjusting it to pH 8.0 by using a sodium hydroxide solution, 2,000 ml of an aqueous solution of tetrachloroauric (III) acid was prepared. To this aqueous solution, 10 g of titanium oxide (Brand Name: titania P-25, manufactured by Japan Aerosil Ltd.) was added, and stirred for one hour so as to suspend the titanium oxide, while gold deposition was immobilized on the surface thereof.

Thereafter, the suspension was filtered, and the remaining matter through filtration was washed by water. After the remaining matter had been vacuum dried at room temperature for twelve hours, it was calcined at 400° C. in the air for four hours so that a titanium oxide having gold deposited thereon (70 mesh to 120 mesh) that was to be used for comparative purpose was prepared. In other words, the titanium oxide having gold deposited thereon was prepared without using silicon oxide or aluminum oxide as a carrier.

Next, the performance of the comparative gold-titania catalyst was examined with respect to a partially-oxidizing reaction for propane. In other words, 0.5 g of the comparative gold-titania catalyst was loaded into a glass reaction cell with a 10 mm inside diameter. Meanwhile, a material gas was prepared by mixing propane, hydrogen, oxygen and argon so as to have a volumetric ratio of 10/10/10/70 (propane/hydrogen/oxygen/argon). After the layer of the comparative gold-titania catalyst had been heated to a temperature of 80° C. by a hot bath, the material gas was passed through the reaction cell at a flow rate of 2,000 ml/hr (standard state) under normal pressure so as to allow propane to react at 80° C.

Thirty minutes after the start of the reaction, the resultant production gas was sampled at the exit of the reaction cell, and the composition was analyzed by gas chromatography. As a result, the conversion of propane was 0.21%, the selectivity to acetone, which is a ketone, was 14.6%, and the space time yield of propane to acetone was 0.3 g/hr/kg·cat.

Comparative Example 3

Reactions, analyses, etc. were implemented in the same manner as those of Comparative Example 2, except that isobutane was used in place of propane in the partially-oxidizing reaction for hydrocarbon in Comparative Example 2. As a result, the conversion of isobutane was 0.39%, the selectivity to t-butyl alcohol which is an alcohol was 46.0%, and the selectivity to acetone which is a ketone was 10.0%. The results showed that the space time yield of isobutane to t-butyl alcohol was 2.4 g/hr/kg·cat.

EXAMPLE 10

First, 900 ml of an aqueous solution containing 0.34 g of chloroauric acid was heated to 70° C., and adjusted to pH 9.5 by using a potassium hydroxide solution. Then, while stirring this aqueous solution, 20 g of the silicon oxide having titanium oxide deposited thereon (the carrier amount of titanium oxide: 1% by weight), which had been obtained through the same processes as Example 6, was added and the solution was stirred at 70° C. for one hour.

Next, supernatant liquid was removed from the aqueous solution containing solid matter, and the resultant solid matter was washed three times by 1,000 ml of water, and then filtered. Thereafter, the solid matter thus filtered was dried at 120° C. for 12 hours, and then calcined at 400° C. in the air for three hours so that a gold-titania-silica catalyst, which is a catalyst consisting of titania-silica having ultrafine gold particles deposited thereon, was obtained.

Next, 1-butene, which serves as an unsaturated hydrocarbon, was partially oxidized by using the gold-titania-silica catalyst. In other words, 2 g of the gold-titania-silica catalyst was loaded into a glass reaction vessel with a 10 mm inside diameter. Next, in a state in which the temperature of the catalyst layer was heated to 190° C. under normal pressure, a mixed gas consisting of hydrogen, oxygen, 1-butene and argon with a volumetric ratio of 20/5/20/55 (hydrogen/oxygen/1-butene/argon) was passed through the reaction vessel at a flow rate of 8,000 ml/hr so as to carry out reaction.

Twenty minutes after the start of the reaction, the resultant production gas was sampled at the exit of the reaction cell, and the composition was analyzed by gas chromatography. As a result, the yield of 1,2-epoxybutane, which is a corresponding epoxide, was 2.4% and the conversion of hydrogen was 22.0% and the space time yield of 1,2-epoxybutane was 61.7 g/hr/kg·cat.

EXAMPLE 11

Cis-2-butene, which serves as an unsaturated hydrocarbon, was partially oxidized by using the gold-titania-silica catalyst that had been prepared in Example 10. In other words, 2 g of the gold-titania-silica catalyst was loaded into a glass reaction vessel with a 10 mm inside diameter. Next, in a state in which the temperature of the catalyst layer was heated to 180° C. under normal pressure, a mixed gas consisting of hydrogen, oxygen, cis-2-butene and argon with a volumetric ratio of 20/5/20/55 (hydrogen/oxygen/cis-2-butene/argon) was passed through the reaction vessel at a flow rate of 8,000 ml/hr so as to carry out reaction.

Twenty minutes after the start of the reaction, the resultant production gas was sampled at the exit of the reaction cell, and the composition was analyzed by gas chromatography. As a result, the yield of 2,3-epoxybutane, which is a corresponding epoxide, was 3.6% and the conversion of hydrogen was 31.8% and the space time yield of 2,3-epoxybutane was 92.6 g/hr/kg·cat.

EXAMPLE 12

Trans-2-butene, which serves as an unsaturated hydrocarbon, was partially oxidized by using the gold-titania-silica catalyst that had been prepared in Example 10. In other words, 2 g of the gold-titania-silica catalyst was loaded into a glass reaction vessel with a 10 mm inside diameter. Next, in a state in which the temperature of the catalyst layer was heated to 190° C. under normal pressure, a mixed gas consisting of hydrogen, oxygen, trans-2-butene and argon with a volumetric ratio of 20/5/20/55 (hydrogen/oxygen/trans-2-butene/argon) was passed through the reaction vessel at a flow rate of 8,000 ml/hr so as to carry out reaction.

Twenty minutes after the start of the reaction, the resultant production gas was sampled at the exit of the reaction cell, and the composition was analyzed by gas chromatography. As a result, the yield of 2,3-epoxybutane, which is a corresponding epoxide, was 5.1%, and the conversion of hydrogen was 25.0% and the space time yield of 2,3-epoxybutane was 131.1 g/hr/kg·cat.

EXAMPLE 13

Cyclohexene, which serves as an unsaturated hydrocarbon, was partially oxidized by using the gold-titania-silica catalyst that had been prepared in Example 10. In other words, 1 g of the gold-titania-silica catalyst was loaded into a stainless reaction vessel with an 8 mm inside diameter. Next, in a state in which the temperature of the catalyst layer was heated to 190° C. under normal pressure, a mixed gas consisting of hydrogen, oxygen, cyclohexene and argon with a volumetric ratio of 18.7/18.7/8.6/54 (hydrogen/oxygen/cyclohexene/argon) was passed through the reaction vessel at a flow rate of 8,000 ml/hr so as to carry out reaction.

Twenty minutes after the start of the reaction, the resultant production gas was sampled at the exit of the reaction cell, and the composition was analyzed by gas chromatography. As a result, the yield of cyclohexene oxide, which is a corresponding epoxide, was 1.7%, and the conversion of hydrogen was 14.1% and the space time yield of cyclohexene oxide was 51.2 g/hr/kg·cat.

EXAMPLE 14

First, 900 ml of an aqueous solution containing 0.34 g of chloroauric acid was heated to 70° C., and adjusted to pH 9.5 by using a cesium hydroxide solution. Then, while stirring this aqueous solution, 20 g of the silicon oxide having titanium oxide deposited thereon (the carrier amount of titanium oxide: 1% by weight), which had been obtained through the same processes as Example 1, was added and the solution was stirred at 70° C. for one hour.

Next, supernatant liquid was removed from the aqueous solution containing solid matter, and the resultant solid matter was washed three times by 1,000 ml of water, and then filtered. Thereafter, the solid matter thus filtered was dried at 120° C. for 12 hours, and then calcined at 400° C. in the air for three hours so that a gold-titania-silica catalyst, which is a catalyst consisting of titania-silica having ultrafine gold particles deposited thereon, was obtained.

Next, isobutylene, which serves as an unsaturated hydrocarbon, was partially oxidized by using the gold-titania-silica catalyst. In other words, 2 g of the gold-titania-silica catalyst was loaded into a glass reaction vessel with a 10 mm inside diameter. Next, in a state in which the temperature of the catalyst layer was heated to 180° C. under normal pressure, a mixed gas consisting of hydrogen, oxygen, isobutylene and argon with a volumetric ratio of 20/5/20/55 (hydrogen/oxygen/isobutylene/argon) was passed through the reaction vessel at a flow rate of 8,000 ml/hr so as to carry out reaction.

Twenty minutes after the start of the reaction, the resultant production gas was sampled at the exit of the reaction cell, and the composition was analyzed by gas chromatography. As a result, the yield of 2-methyl-1,2-epoxypropane, which is a corresponding epoxide, was 1.4%, and the conversion of hydrogen was 6.1% and the space time yield of 2-methyl-1,2-epoxypropane was 36.0 g/hr/kg·cat.

EXAMPLE 15

1,3-butadiene, which serves as an unsaturated hydrocarbon, was partially oxidized by using the gold-titania-silica catalyst that had been prepared in Example 14. In other words, 1 g of the gold-titania-silica catalyst was loaded into a stainless reaction vessel with an 8 mm inside diameter. Next, in a state in which the temperature of the catalyst layer was heated to 215° C. under normal pressure, a mixed gas consisting of hydrogen, oxygen, 1,3-butadiene and argon with a volumetric ratio of 17/17/17/49 (hydrogen/oxygen/1,3-butadiene/argon) was passed through the reaction vessel at a flow rate of 9,000 ml/hr so as to carry out reaction.

Twenty minutes after the start of the reaction, the resultant production gas was sampled at the exit of the reaction cell, and the composition was analyzed by gas chromatography. As a result, the yield of 3,4-epoxy-1-butene which is a corresponding epoxide, was 1.3%, and the conversion of hydrogen was 4.8% and the space time yield of 3,4-epoxy-1-butene was 62.2 g/hr/kg·cat.

EXAMPLE 16

In 150 ml of a methanol solution containing 3.28 g of titanylacetylacetonate (manufactured by Dojindo Laboratories Co., Ltd.), 100 g of silica serving as a carrier (Brand Name: CARIACT Q-10, manufactured by Fujisilysia Chemical, Ltd.; specific surface area 326 $m^2/g$; globular particles with 0.84 mm to 1.7 mm in diameter) was immersed, and then the methanol was distilled and removed until the surface of silica was completely dried out, while stirring in a hot bath. The remaining solid matter was dried at 120° C. for 12 hours, and then calcined at 600° C. in the air for three hours so that a silica carrier having titania deposited thereon was obtained. With respect to the carrier, the carrier amount of the titania was 1% by weight.

Next, 2,000 ml of an aqueous solution containing 0.69 g of chloroauric acid was heated to 70° C., and adjusted to pH 9 by using a sodium hydroxide solution. Then, while stirring the solution, 40 g of the above-mentioned silica having titania deposited thereon was added to it, and after the solution had been stirred at 70° C. for one hour, the resultant suspension was left standing at rest so that solid matter was deposited.

Next, supernatant liquid was removed from the aqueous solution containing solid matter, and the resultant solid matter was washed three times by 1000 ml of water, and then filtered. Then, the undried solid matter was divided into four, thereby obtaining four portions of solid matter (hereinafter, referred to as solid matter (1)).

Next, the following processes were carried out on one portion of solid matter (1). Solid matter (1) was immersed into an aqueous solution containing 0.115 g of sodium carbonate, and water was expelled therefrom by distillation until the surface of the solid matter was completely dried out, while stirring in a hot bath. After the solid matter had been further dried at 120° C. for twelve hours, it was calcined at 400° C. in the air for three hours so that a catalyst in which ultrafine gold particles are deposited on the silica carrier having titania deposited thereon (hereinafter, referred to as catalyst (A)) was obtained.

The contents of sodium and gold contained in catalyst (A), when analyzed by the fluorescence X-ray spectroscopy, were 0.585% by weight and 0.148% by weight respectively.

EXAMPLE 17

Another portion of solid matter (1) obtained in Example 16 was immersed into an aqueous solution containing 0.046 g of sodium carbonate, and water was expelled therefrom by distillation until the surface of the solid matter was completely dried out, while stirring in a hot bath. After the solid matter had been further dried at 120° C. for twelve hours, it was calcined at 400° C. in the air for three hours so that a catalyst in which ultrafine gold particles are deposited on the silica carrier having titania deposited thereon (hereinafter, referred to as catalyst (B)) was obtained.

The contents of sodium and gold contained in catalyst (B), when analyzed by the fluorescence X-ray spectroscopy, were 0.292% by weight and 0.150% by weight respectively.

EXAMPLE 18

Still another portion of solid matter (1) obtained in Example 16 was dried at 120° C. for twelve hours, and then calcined at 400° C. in the air for three hours so that a catalyst in which ultrafine gold particles are deposited on the silica carrier having titania deposited thereon (hereinafter, referred to as catalyst (C)) was obtained.

The contents of sodium and gold contained in catalyst (C), when analyzed by the fluorescence X-ray spectroscopy, were 0.115% by weight and 0.153% by weight respectively.

EXAMPLE 19

The other portion of solid matter (1) obtained in Example 16 was washed three times with 300 ml of an aqueous solution of carbonate at pH 4, and further washed one time with 300 ml of water. Thereafter, the solid matter thus washed was dried at 120° C. for twelve hours, and then calcined at 400° C. in the air for three hours so that a catalyst in which ultrafine gold particles are deposited on the silica carrier having titania deposited thereon (hereinafter, referred to as catalyst (D)) was obtained.

When the contents of sodium and gold contained in catalyst (D) were analyzed by the fluorescence X-ray spectroscopy, the content of gold was 0.153% by weight, but no sodium was detected.

EXAMPLE 20

Trans-2-butene, which serves as a hydrocarbon of the olefin family, was partially oxidized by using catalyst (A) obtained in Example 16. In other words, 1 g of catalyst (A) was loaded into a glass reaction vessel with a 10 mm inside diameter; thus, a catalyst layer was prepared. Next, in a state in which the temperature of the catalyst layer was heated to 180° C. (that is, at a reaction temperature of 180° C.), a mixed gas consisting of hydrogen, oxygen, trans-2-butene and argon with a volumetric ratio of 20/5/20/55 (hydrogen/oxygen/trans-2-butene/argon) was passed through the reaction vessel at a flow rate of 4,000 ml/hr so as to carry out reaction.

Thirty minutes after the start of the reaction, the resultant production gas was sampled at the exit of the reaction vessel, and the composition was analyzed by gas chromatography. As a result, the conversion of trans-2-butene was 4.4%, the selectivity of 2,3-epoxybutane, which is a corresponding epoxide, was 96%, the conversion of hydrogen was 15.8%, and the space time yield of 2,3-epoxybutane was 108.6 g/hr per 1 kg of catalyst and 73.4 g/hr per 1 g of gold. The results including the contents of sodium and gold in the catalyst are shown in Table 1.

Moreover, fifty hours after the start of the reaction, the resultant production gas was sampled at the exit of the reaction vessel, and the composition was analyzed by gas chromatography. As a result, it was found that the space time yield of 2,3-epoxybutane per 1 kg of catalyst decreased by 29% as compared with the space time yield thirty minutes after the start of the reaction, that is, 71% of the space time yield thirty minutes after thereof.

EXAMPLE 21

Trans-2-butene was partially oxidized by using catalyst (B) obtained in Example 17 in the same processes as those of Example 20. The results including the contents of sodium and gold in the catalyst are shown in Table 1.

EXAMPLE 22

Trans-2-butene was partially oxidized by using catalyst (C) obtained in Example 18 in the same processes as those of Example 20. The results including the contents of sodium and gold in the catalyst are shown in Table 1.

EXAMPLE 23

Trans-2-butene was partially oxidized by using catalyst (D) obtained in Example 19 in the same processes as those of Example 20. The results including the contents of sodium and gold in the catalyst are shown in Table 1.

Moreover, twenty hours after the start of the reaction, the resultant production gas was sampled at the exit of the reaction vessel, and the composition was analyzed by gas chromatography. As a result, it was found that the space time yield of 2,3-epoxybutane per 1 kg of catalyst decreased by 52% as compared with the space time yield thirty minutes after the start of the reaction, that is, 48% of the space time yield thirty minutes after thereof.

TABLE 1

| | EXAMPLE 20 | EXAMPLE 21 | EXAMPLE 22 | EXAMPLE 23 |
|---|---|---|---|---|
| Catalyst | (A) | (B) | (C) | (D) |
| Content of Na in Catalyst | 0.585 Weight % | 0.292 Weight % | 0.115 Weight % | No detection |
| Content of Au in Catalyst | 0.148 Weight % | 0.150 Weight % | 0.153 Weight % | 0.153 Weight % |
| Conversion of trans-2-butene | 4.4% | 4.7% | 3.9% | 1.8% |
| Selectivity of 2,3-epoxybutane | 96% | 95% | 95% | 60% |
| Conversion of Hydrogen | 15.8% | 17.5% | 12.9% | 9.2% |
| Space Time Yield of 2,3-epoxybutane Per 1 kg of Catalyst | 108.6 g/hr | 114.8 g/hr | 95.2 g/hr | 27.7 g/hr |
| Space Time Yield of 2,3-epoxybutane Per 1 g of Au | 73.4 g/hr | 76.5 g/hr | 62.3 g/hr | 18.1 g/hr |

EXAMPLE 24

In 150 ml of a methanol solution containing 3.28 g of titanylacetylacetonate (manufactured by Dojindo Laboratories Co., Ltd.), 100 g of silica serving as a carrier (Brand Name: CARIACT Q-15, manufactured by Fujisilysia Chemical, Ltd.; specific surface area 196 $m^2/g$; globular particles with 0.84 mm to 1.7 mm in diameter) was immersed, and then the methanol was distilled and removed until the surface of silica was completely dried out, while stirring in a hot bath. The remaining solid matter was dried at 120° C. for 12 hours, and then calcined at 600° C. in the air for three hours so that a silica carrier having titania deposited thereon was obtained. With respect to the carrier, the carrier amount of the titania was 1% by weight.

Next, 4,000 ml of an aqueous solution containing 0.69 g of chloroauric acid was heated to 70° C., and adjusted to pH 9 by using a sodium hydroxide solution. Then, while stirring the solution, 40 g of the above-mentioned silica having titania deposited thereon was added to it, and after the solution had been stirred at 70° C. for one hour, the resultant suspension was left standing at rest so that solid matter was deposited.

Next, supernatant liquid was removed from the aqueous solution containing solid matter, and the resultant solid matter was washed three times by 2,000 ml of water, and then filtered. Then, the undried solid matter was divided into four, thereby obtaining four portions of solid matter (hereinafter, referred to as solid matter (2)).

Next, the following processes were carried out on one portion of solid matter (2). Solid matter (2) was washed three times by using 300 ml of an aqueous solution of sodium hydroxide with pH 10, and then washed once by using 300 ml of water. After the solid matter had been further dried at 120° C. for twelve hours, it was calcined at 400° C. in the air for three hours so that a catalyst in which ultrafine gold particles are deposited on the silica carrier having titania deposited thereon (hereinafter, referred to as catalyst (E)) was obtained.

The contents of sodium and gold contained in catalyst (E), when analyzed by the fluorescence X-ray spectroscopy, were 0.091% by weight and 0.056% by weight respectively.

EXAMPLE 25

Another portion of solid matter (2) obtained in Example 24 was washed once by using an aqueous solution of sodium hydroxide with pH 10, and then washed once by using 300 ml of water. After the solid matter had been further dried at 120° C. for twelve hours, it was calcined at 400° C. in the air for three hours so that a catalyst in which ultrafine gold particles are deposited on the silica carrier having titania deposited thereon (hereinafter, referred to as catalyst (F)) was obtained.

The contents of sodium and gold contained in catalyst (F), when analyzed by the fluorescence X-ray spectroscopy, were 0.083% by weight and 0.060% by weight respectively.

EXAMPLE 26

Still another portion of solid matter (2) obtained in Example 24 was dried at 120° C. for twelve hours, and then calcined at 400° C. in the air for three hours so that a catalyst in which ultrafine gold particles are deposited on the silica carrier having titania deposited thereon (hereinafter, referred to as catalyst (G)) was obtained.

The contents of sodium and gold contained in catalyst (G), when analyzed by the fluorescence X-ray spectroscopy, were 0.033% by weight and 0.070% by weight respectively.

EXAMPLE 27

Still another portion of solid matter (2) obtained in Example 24 was washed three times with an aqueous solution of carbonate at pH 4, and further washed one time with 300 ml of water. Thereafter, the solid matter thus washed was dried at 120° C. for twelve hours, and then calcined at 400° C. in the air for three hours so that a catalyst in which ultrafine gold particles are deposited on the silica carrier having titania deposited thereon (hereinafter, referred to as catalyst (H)) was obtained.

When the contents of sodium and gold contained in catalyst (H) were analyzed by the fluorescence X-ray spectroscopy, the content of gold was 0.069% by weight, but no sodium was detected.

EXAMPLE 28

Propylene, which serves as a hydrocarbon of the olefin family, was partially oxidized by using catalyst (E) obtained in Example 24. In other words, 1 g of catalyst (E) was loaded into a glass reaction vessel with a 10 mm inside diameter; thus, a catalyst layer was prepared. Next, in a state in which the temperature of the catalyst layer was heated to 180° C. (that is, at a reaction temperature of 180° C.), a mixed gas consisting of hydrogen, oxygen, propylene and argon with a volumetric ratio of 20/5/20/55 (hydrogen/oxygen/propylene/argon) was passed through the reaction vessel at a flow rate of 8,000 ml/hr so as to carry out reaction.

Thirty minutes after the start of the reaction, the resultant production gas was sampled at the exit of the reaction vessel, and the composition was analyzed by gas chromatography. As a result, the conversion of propylene was 1.5%, the selectivity of propyleneoxide, which is a corresponding epoxide, was 96%, the conversion of hydrogen was 5.1%, and the space time yield of propyleneoxide was 59.6 g/hr per 1 kg of catalyst and 106.6 g/hr per 1 g of gold. The results including the contents of sodium and gold in the catalyst are shown in Table 2.

EXAMPLE 29

Propylene was partially oxidized by using catalyst (F) obtained in Example 25 in the same processes as those of Example 28. The results including the contents of sodium and gold in the catalyst are shown in Table 2.

EXAMPLE 30

Propylene was partially oxidized by using catalyst (G) obtained in Example 26 in the same processes as those of Example 28. The results including the contents of sodium and gold in the catalyst are shown in Table 2.

EXAMPLE 31

Propylene was partially oxidized by using catalyst (H) obtained in Example 27 in the same processes as those of Example 28. The results including the contents of sodium and gold in the catalyst are shown in Table 2.

TABLE 2

|  |  | EXAMPLE 28 | EXAMPLE 29 | EXAMPLE 30 | EXAMPLE 31 |
|---|---|---|---|---|---|
| Catalyst | | (E) | (F) | (G) | (H) |
| Content of Na in Catalyst | | 0.091 Weight % | 0.083 Weight % | 0.033 Weight % | No detection |
| Content of Au in Catalyst | | 0.056 Weight % | 0.060 Weight % | 0.070 Weight % | 0.069 Weight % |
| Conversion of propylene | | 1.5% | 1.2% | 1.1% | 0.4% |
| Selectivity of propylene oxide | | 96% | 96% | 92% | 41% |
| Conversion of Hydrogen | | 5.1% | 5.2% | 4.4% | 2.7% |
| Space Time Yield of propylene oxide | Per 1 kg of Catalyst | 59.6 g/hr | 47.8 g/hr | 42.0 g/hr | 6.8 g/hr |
| | Per 1 g of Au | 106.6 g/hr | 79.6 g/hr | 59.8 g/hr | 9.8 g/hr |

EXAMPLE 32

In 150 ml of a methanol solution containing 3.28 g of titanylacetylacetonate (manufactured by Dijindo Laboratories Co., Ltd.), 100 g of silica serving as a carrier (Brand Name: CARIACT Q-10, manufactured by Fujisilysia Chemical, Ltd.; specific surface area 326 m$^2$/g; globular particles with 0.84 mm to 1.7 mm in diameter) was immersed, and then the methanol was distilled and removed until the surface of silica was completely dried out, while stirring in a hot bath. The remaining solid matter was dried at 120° C. for 12 hours, and then calcined at 600° C. in the air for three hours so that a silica carrier having titania deposited thereon (hereinafter, referred to as a silica carrier having titania deposited thereon) was obtained. With respect to the carrier, the carrier amount of the titania was 1% by weight.

Next, 2,000 ml of an aqueous solution containing 0.69 g of chloroauric acid was heated to 70° C, and adjusted to pH 9 by using a cesium hydroxide solution. Then, while stirring the solution, 40 g of the above-mentioned silica having titania deposited thereon was added to it, and after the solution had been stirred at 70° C. for one hour, the resultant suspension was left standing at rest so that solid matter was deposited.

Next, supernatant liquid was removed from the aqueous solution containing solid matter, and the resultant solid matter was washed three times by 1,000 ml of water, and then filtered. Then, the undried solid matter was divided into three, thereby obtaining three portions of solid matter (hereinafter, referred to as solid matter (3)).

Next, the following processes were carried out on one portion of solid matter (3). Solid matter (3) was immersed into an aqueous solution containing 0.319 g of cesium carbonate, and water was expelled therefrom by distillation until the surface of the solid matter was completely dried out, while stirring in a hot bath. After the solid matter had been further dried at 120° C. for twelve hours, it was calcined at 400° C. in the air for three hours so that a catalyst in which ultrafine gold particles are deposited on the silica carrier having titania deposited thereon (hereinafter, referred to as catalyst (I)) was obtained.

The contents of cesium and gold contained in catalyst (I), when analyzed by the fluorescence X-ray spectroscopy, were 5.032% by weight and 0.117% by weight respectively.

EXAMPLE 33

Another portion of solid matter (3) obtained in Example 32 was dried at 120° C. for twelve hours, and then calcined at 400° C. in the air for three hours so that a catalyst in which ultrafine gold particles are deposited on the silica carrier having titania deposited thereon (hereinafter, referred to as catalyst (J)) was obtained.

The contents of cesium and gold contained in catalyst (J), when analyzed by the fluorescence X-ray spectroscopy, were 0.715% by weight and 0.162% by weight respectively.

EXAMPLE 34

Still another portion of solid matter (3) obtained in Example 32 was washed three times with 300 ml of an aqueous solution of carbonic acid at pH4, and then washed once with 300 ml of water. After, the solid matter thus washed had been dried at 120° C. in the air for twelve hours, it was calcined at 400° C. in the air for three hours so that a catalyst in which ultrafine gold particles are deposited on the silica carrier having titania deposited thereon (hereinafter, referred to as catalyst (K)) was obtained.

When the contents of cesium and gold contained in catalyst (K) were analyzed by the fluorescence X-ray spectroscopy, it was found that the content of gold was 0.162% by weight but no cesium was detected.

EXAMPLE 35

Isobutylene, which serves as a hydrocarbon of the olefin family, was partially oxidized by using catalyst (I) obtained in Example 32. In other words, 1 g of catalyst (I) was loaded into a glass reaction vessel with a 10 mm inside diameter; thus, a catalyst layer was prepared. Next, in a state in which the temperature of the catalyst layer was heated to 140° C. (that is, at a reaction temperature of 140° C.), a mixed gas consisting of hydrogen, oxygen, isobutylene and argon with a volumetric ratio of 20/5/20/55 (hydrogen/oxygen/isobutylene/argon) was passed through the reaction vessel at a flow rate of 8,000 ml/hr so as to carry out reaction.

Thirty minutes after the start of the reaction, the resultant production gas was sampled at the exit of the reaction vessel, and the composition was analyzed by gas chromatography. As a result, the conversion of isobutylene was 1.0%, the selectivity of 2-methyl-1,2-epoxypropane, which is a corresponding epoxide, was 15%, the conversion of hydrogen was 1.3%, and the space time yield of 2-methyl-1,2-epoxypropane was 7.7 g/hr per 1 kg of catalyst and 6.6 g/hr per 1 g of gold. The results including the contents of cesium and gold in the catalyst are shown in Table 3.

EXAMPLE 36

Isobutylene was partially oxidized by using catalyst (J) obtained in Example 33 in the same processes as those of Example 35. The results including the contents of cesium and gold in the catalyst are shown in Table 3.

EXAMPLE 37

Isobutylene was partially oxidized by using catalyst (K) obtained in Example 34 in the same processes as those of Example 35. The results including the contents of cesium and gold in the catalyst are shown in Table 3.

TABLE 3

| | | EXAMPLE 35 | EXAMPLE 36 | EXAMPLE 37 |
|---|---|---|---|---|
| Catalyst | | (I) | (J) | (K) |
| Content of Cs in Catalyst | | 5.032 Weight % | 0.715 Weight % | No detection |
| Content of Au in Catalyst | | 0.117 Weight % | 0.162 Weight % | 0.162 Weight % |
| Conversion of isobutylene | | 1.0% | 1.4% | 0.3% |
| Selectivity of 2-methyl-1,2-epoxypropane | | 15% | 51% | 0% |
| Conversion of Hydrogen | | 1.3% | 6.1% | 1.8% |
| Space Time Yield of 2-methyl-1,2-epoxypropane | Per 1 kg of Catalyst | 7.7 g/hr | 36.7 g/hr | 0 g/hr |
| | Per 1 g of Au | 6.6 g/hr | 22.7 g/hr | 0 g/hr |

EXAMPLE 38

Next, 2,000 ml of an aqueous solution containing 0.69 g of chloroauric acid was heated to 70° C., and adjusted to pH 9 by using a potassium hydroxide solution. Then, while stirring the solution, 40 g of the above-mentioned silica carrier having titania deposited thereon, obtained in Example 32, was added to it, and after the solution had been stirred at 70° C. for one hour, the resultant suspension was left standing at rest so that solid matter was deposited.

Then, supernatant liquid was removed from the aqueous solution containing solid matter, and the resultant solid matter was washed three times by 500 ml of water, and then filtered. Then, the undried solid matter was divided into two, thereby obtaining two portions of solid matter (hereinafter, referred to as solid matter (4)).

After one portion of solid matter (4) had been further dried at 120° C. for twelve hours, it was calcined at 400° C. in the air for three hours so that a catalyst in which ultrafine gold particles are deposited on the silica carrier having titania deposited thereon (hereinafter, referred to as catalyst (L)) was obtained.

The contents of potassium and gold contained in catalyst (L), when analyzed by the fluorescence X-ray spectroscopy, were 0.221% by weight and 0.171% by weight respectively.

EMBODIMENT 39

Another portion of solid matter (4) obtained in Example 38 was washed three times by using 500 ml of an aqueous solution of carbonic acid with pH 4, and then washed once by using 500 ml of water. After the solid matter had been dried at 120° C. for twelve hours, it was calcined at 400° C. in the air for three hours so that a catalyst in which ultrafine gold particles are deposited on the silica carrier having titania deposited thereon (hereinafter, referred to as catalyst (M)) was obtained.

When the contents of potassium and gold contained in catalyst (M) analyzed by the fluorescence X-ray spectroscopy, the content of gold was 0.170% by weight but no potassium was detected.

EXAMPLE 40

1-Hexene, which serves as a hydrocarbon of the olefin family, was partially oxidized by using catalyst (L) obtained in Example 38. In other words, 1 g of catalyst (L) was loaded into a glass reaction vessel with a 10 mm inside diameter; thus, a catalyst layer was prepared. Next, in a state in which the temperature of the catalyst layer was heated to 190° C. (that is, at a reaction temperature of 190° C.), a mixed gas consisting of hydrogen, oxygen, 1-hexene and helium with a volumetric ratio of 19/19/7/55 (hydrogen/oxygen/1-hexene/helium) was passed through the reaction vessel at a flow rate of 3,230 ml/hr so as to carry out reaction.

Thirty minutes after the start of the reaction, the resultant production gas was sampled at the exit of the reaction vessel, and the composition was analyzed by gas chromatography. As a result, the conversion of 1-hexene was 2.8%, the selectivity of 1,2-epoxyhexane, which is a corresponding epoxide, was 82%, and the conversion of hydrogen was 3.9%.

EXAMPLE 41

1-Hexene was partially oxidized by using catalyst (M) obtained in Example 39 in the same processes as those of Example 40. As a result, the conversion of 1-hexene was 1.7%, the selectivity of 1,2-expoxyhexane was 68%, and the conversion of hydrogen was 2.8%.

EXAMPLE 42

In 100 ml of a methanol solution containing 0.65 g of titanylacetylacetonate (manufactured by Dojindo Laboratories Co., Ltd.) and 0.024 g of magnesium acetylacetonate 2 hydrate (manufactured by Kishida Co., Ltd.), 20 g of silica serving as a carrier (Brand Name: CARIACT Q-10, manufactured by Fujisilysia Chemical, Ltd.; specific surface area 326 m²/g; globular particles having a diameter ranging 0.84 mm to 1.7 mm) was immersed, and then the methanol was distilled and removed until the surface of silica was completely dried out, while stirring in a hot bath.

The remaining solid matter was dried at 120° C. for 12 hours, and then calcined at 800° C. in the air for three hours so that a silica carrier having titania and magnesia deposited thereon was obtained. With respect to the carrier, the carrier amount of the titania was 1% by weight and the carrier amount of the magnesia was 0.025% by weight.

Next, 900 ml of an aqueous solution containing 0.34 g of chloroauric acid was heated to 70° C., and adjusted to pH 9 by using a sodium hydroxide solution. Then, while stirring the solution, 20 g of the above-mentioned silica carrier was added to it, and after the solution had been stirred at 70° C. for one hour, the resultant suspension was left standing at rest so that solid matter was deposited.

Next, supernatant liquid was removed from the aqueous solution containing solid matter, and the resultant solid matter was washed three times by 1,000 ml of water, and then filtered. Thereafter, the solid matter thus filtered was dried at 120° C. for 12 hours, and then calcined at 400° C. in the air for three hours so that a gold/titania-magnesia/silica catalyst, which is a catalyst consisting of a silica carrier which had titania-magnesia deposited thereon and onto which gold was deposited, was obtained.

EXAMPLE 43

Propylene, which serves as a hydrocarbon of the olefin family, was partially oxidized by using the gold/titania-magnesia/silica catalyst obtained in Example 42. In other words, 1 g of the gold/titania-magnesia/silica catalyst was loaded into a glass reaction vessel with a 10 mm inside diameter; thus, a catalyst layer was prepared. Next, in a state in which the temperature of the catalyst layer was heated to 180° C. (that is, at a reaction temperature of 180° C.), a mixed gas consisting of hydrogen, oxygen, propylene and argon with a volumetric ratio of 10/10/10/70 (hydrogen/oxygen/propylene/argon) was passed through the reaction vessel at a flow rate of 4,000 ml/hr.

Thirty minutes after the start of the reaction, the resultant production gas was sampled at the exit of the reaction vessel, and the composition was analyzed by gas chromatography. As a result, the conversion of propylene was 7.3%, the selectivity of propyleneoxide, which is a corresponding epoxide, was 92.6%, the conversion of hydrogen was 16.8%, the yield of propyleneoxide was 6.8%, and the space time yield of propyleneoxide was 70.4 g/hr per 1 kg of catalyst.

EXAMPLE 44

The same processes as those of Example 42 were carried out except that instead of using 100 ml of a methanol solution containing 0.65 g of titanylacetylacetonate and 0.024 g of magnesium acetylacetonate 2 hydrate, 100 ml of a methanol solution containing 0.65 g of titanylacetylacetonate was used; thus, a gold/titania/silica catalyst was obtained.

EXAMPLE 45

Propylene was partially oxidized in the same manner as Example 43 except that instead of using the gold/titania-magnesia/silica catalyst of Example 43, the gold/titania/silica catalyst without magnesium added thereto, obtained in Example 44, was used.

Thirty minutes after the start of the reaction, the resultant production gas was sampled at the exit of the reaction vessel, and the composition was analyzed by gas chromatography. As a result, the conversion of propylene was 5.8%, the selectivity of propyleneoxide, which is a corresponding epoxide, was 94.4%, the conversion of hydrogen was 15.9%, the yield of propyleneoxide was 5.5%, and the space time yield of propyleneoxide was 57.0 g/hr per 1 kg of catalyst.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

POTENTIAL FOR INDUSTRIAL USE

As described earlier, the first partially-oxidizing catalyst for a hydrocarbon of the present invention has a composition containing gold, titanium oxide and a carrier whose specific surface area is not less than 50 m$^2$/g. With this composition, it is possible to provide a partially-oxidizing catalyst for a hydrocarbon with superior activity and selectivity.

As described earlier, in the first partially-oxidizing catalyst, the carrier is preferably made from silicon oxide and/or aluminum oxide. Further, as described earlier, in the first partially-oxidizing catalyst, the content of gold is preferably set in the range of 0.005 to 5% by weight. As described earlier, in the first partially-oxidizing catalyst, the content of titanium oxide is set in the range of 0.1 to 20% by weight. With these compositions, it becomes possible to provide a partially-oxidizing catalyst which can carry out partial oxidation effectively.

As described earlier, the second partially-oxidizing catalyst for a hydrocarbon of the present invention has a composition containing gold, a titanium-containing oxide and at least one element selected from the group consisting of an alkaline metal, an alkaline earth metal and thallium.

With this composition, it is possible to provide a partially-oxidizing catalyst for a hydrocarbon which has superior activity and selectivity in a reaction for partially oxidizing the hydrocarbon in the presence of hydrogen and oxygen. In addition, with the above-mentioned composition, the one element, selected from the group consisting of alkaline metal, alkaline-earth metal and thallium, makes it possible to suppress deterioration with time, thereby providing a catalyst having superior stability in life time.

As described earlier, the first and second partially-oxidizing methods for a hydrocarbon of the present invention is a method for partially oxidizing the hydrocarbon by using the first and second partially-oxidizing catalyst respectively in the presence of hydrogen and oxygen.

In accordance with the first and second partially-oxidizing methods, it is possible to carry out a partially-oxidizing reaction for a hydrocarbon with high selectivity and high conversion. Consequently, an alcohol and/or a ketone can be obtained from a saturated hydrocarbon with high selectivity and high conversion, and an epoxide can be obtained from a hydrocarbon of the olefin family (an unsaturated hydrocarbon) with high selectivity and high conversion. Consequently, it is possible to manufacture an epoxide from a hydrocarbon of the olefin family and also to manufacture an alcohol and/or a ketone from a saturated hydrocarbon, effectively by using a simple method.

Moreover, in accordance with the second partially-oxidizing method, since the catalyst having superior stability in life time is utilized, it is possible to carry out a partially oxidizing reaction for a hydrocarbon for a long time in a stable manner.

The above-mentioned first and second partially-oxidizing methods make it possible to effectively manufacture an epoxide from a hydrocarbon of the olefin family (an unsaturated hydrocarbon). Moreover, in the first and second partially-oxidizing methods for a hydrocarbon, propyleneoxide can be manufactured effectively by using propylene as the hydrocarbon.

Furthermore, in the first and second partially-oxidizing methods, hydrocarbon is partially oxidized effectively by setting the reaction temperature in the range of 100° C. to 250° C.

We claim:

1. A partially-oxidizing catalyst for a hydrocarbon comprising gold and titanium oxide on a carrier whose specific surface area is at least 50 m$^2$/g.

2. The partially-oxidizing catalyst for a hydrocarbon as defined in claim 1, wherein the carrier contains silicon oxide and/or aluminum oxide.

3. The partially-oxidizing catalyst for a hydrocarbon as defined in claim 1, wherein the content of gold is set in the range of 0.005 to 5% by weight.

4. The partially-oxidizing catalyst for a hydrocarbon as defined in claim 1, wherein the content of titanium oxide is set in the range of 0.1 to 20% by weight.

5. The partially-oxidizing catalyst for a hydrocarbon as defined in claim 3, wherein the content of titanium oxide is set in the range of 0.1 to 20% by weight.

6. A partially-oxidizing catalyst for a hydrocarbon as defined in claim 1, wherein gold is prepared as ultrafine particles whose diameter is not more than 10 nanometers.

7. A partially-oxidizing catalyst for a hydrocarbon comprising gold, a titanium-containing metal oxide and at least one element selected from the group consisting of an alkaline metal, an alkaline earth metal and thallium.

8. The partially-oxidizing catalyst for a hydrocarbon as defined in claim 7, comprising at least one alkaline metal selected from the group consisting of K, Rb and Cs or at least one alkaline-earth metal selected from the group consisting of Mg, Ca, Sr and Ba.

9. The partially-oxidizing catalyst for a hydrocarbon as defined in claim 7, wherein the total content of the alkaline metal, the alkaline-earth metal and the thallium is set in the range of 0.001 to 20% by weight.

10. The partially-oxidizing catalyst for a hydrocarbon as defined in claim 7, further comprising a carrier whose specific surface area is not less than 50 m$^2$/g.

11. The partially-oxidizing catalyst for a hydrocarbon as defined in claim 7, wherein the carrier contains silicon oxide and/or aluminum oxide.

12. The partially-oxidizing catalyst for a hydrocarbon as defined in claim 7, wherein gold is prepared as ultrafine particles whose diameter is not more than 10 nanometers.

13. The partially-oxidizing catalyst for a hydrocarbon as defined in claim 7, wherein the content of gold is set in the range of 0.005 to 5% by weight.

14. The partially-oxidizing catalyst for a hydrocarbon as defined in claim 7, wherein the titanium-containing metal oxide is titanium oxide.

15. The partially-oxidizing catalyst for a hydrocarbon as defined in claim 7, wherein the content of titanium, when converted into titanium dioxide, is set in the range of 0.1 to 20% by weight.

16. A method for partially-oxidizing a hydrocarbon comprising a step of: adding a hydrocarbon to a mixture of hydrogen and oxygen in the presence of a partially-oxidizing catalyst, where the catalyst comprises gold and titanium oxide on a carrier whose specific surface area is at least 50 m$^2$/g.

17. The partially-oxidizing method for a hydrocarbon as defined in claim 16, wherein the volumetric ratio (hydrogen/hydrocarbon) of hydrogen and hydrocarbon is set in the range of 1/10 to 100/1.

18. The partially-oxidizing method for a hydrocarbon as defined in claim 16, wherein the hydrocarbon is an unsaturated hydrocarbon.

19. The partially-oxidizing method for a hydrocarbon as defined in claim 18, wherein the hydrocarbon is propylene.

20. The partially-oxidizing method for a hydrocarbon as defined in claim 18, wherein the hydrocarbon is an internal olefin.

21. The partially-oxidizing method for a hydrocarbon as defined in claim 16, wherein the hydrocarbon is a saturated hydrocarbon.

22. The partially-oxidizing method for a hydrocarbon as defined in claim 16, wherein the reaction temperature is set in the range of 100° C. to 250° C.

23. A method for partially-oxidizing a hydrocarbon comprising a step of: adding a hydrocarbon to a mixture of hydrogen and oxygen in the presence of a partially-oxidizing catalyst, where the catalyst comprises golds a titanium-containing metal oxide and at least one element selected from the group consisting of an alkaline metal, an alkaline earth metal and thallium.

24. The partially-oxidizing method for a hydrocarbon as defined in claim 23, wherein the volumetric ratio (hydrogen/hydrocarbon) of hydrogen and hydrocarbon is set in the range of 1/10 to 100/1.

25. The partially-oxidizing method for a hydrocarbon as defined in claim 23, wherein the hydrocarbon is a hydrocarbon of the olefin family.

26. The partially-oxidizing method for a hydrocarbon as defined in claim 25, wherein the hydrocarbon of the olefin family is propylene.

27. The partially-oxidizing method for a hydrocarbon as defined in claim 25, wherein the hydrocarbon of the olefin family is an internal olefin.

28. The partially-oxidizing method for a hydrocarbon as defined in claim 23, wherein the hydrocarbon is a saturated hydrocarbon.

29. The partially-oxidizing method for a hydrocarbon as defined in claim 23, wherein the reaction temperature is set in the range of 100° C. to 250° C.

30. A method for preparing a partially-oxidizing catalyst for a hydrocarbon comprising the steps of:
   a. depositing onto a titanium-containing metal oxide, at least one element selected from the group consisting of an alkaline metal, an alkaline earth metal and thallium;
   b. after step a depositing gold onto the titanium-containing metal oxide with the at least one element.

31. A method for preparing a partially-oxidizing catalyst for a hydrocarbon comprising the steps of:
   a. depositing onto a titanium-containing metal oxide, at least one element selected from the group consisting of an alkaline metal, an alkaline earth metal and thallium;
   b. simultaneously with step a, depositing gold onto the titanium-containing metal oxide.

32. The partially-oxidizing catalyst as defined in claim 1, wherein the specific surface area of the carrier is at least 196 $m^2/g$.

33. The partially-oxidizing catalyst for a hydrocarbon as defined in claim 1, wherein the titanium oxide is an amorphous type or a complex material including another oxide.

34. The partially-oxidizing catalyst for a hydrocarbon as defined in claim 33, wherein the another oxide is silicon oxide.

35. The partially-oxidizing catalyst as defined in claim 1, wherein the titanium oxide has a content in a range of 0.1% to 2% by weight.

36. The partially-oxidizing catalyst as defined in claim 3, wherein the titanium oxide has a content in a range of 0.1% to 2% by weight.

37. The method for partially-oxidizing catalyst as defined in claim 16, wherein the mixture of hydrogen, oxygen and the catalyst has a reaction temperature in a range of 140° C. to 250° C.

38. A method as defined in claim 23, wherein the mixture of hydrogen, oxygen and the catalyst has a reaction temperature in the range of 140° C. to 250° C.

* * * * *